(12) United States Patent
Fan et al.

(10) Patent No.: US 6,890,741 B2
(45) Date of Patent: May 10, 2005

(54) MULTIPLEXED DETECTION OF ANALYTES

(75) Inventors: Jian-Bing Fan, San Diego, CA (US); John R. Stuelpnagel, Encinitas, CA (US); Mark S. Chee, Del Mar, CA (US)

(73) Assignee: Illumina, Inc., San Diego, CA (US)

( * ) Notice: Subject to any disclaimer, the term of this patent is extended or adjusted under 35 U.S.C. 154(b) by 131 days.

(21) Appl. No.: 09/915,231

(22) Filed: Jul. 24, 2001

(65) Prior Publication Data

US 2002/0132241 A1 Sep. 19, 2002

Related U.S. Application Data

(63) Continuation-in-part of application No. 09/779,376, filed on Feb. 7, 2001.
(60) Provisional application No. 60/234,143, filed on Sep. 21, 2000, provisional application No. 60/234,732, filed on Sep. 22, 2000, provisional application No. 60/180,810, filed on Feb. 7, 2000, and provisional application No. 60/297,609, filed on Jun. 11, 2001.

(51) Int. Cl.[7] ............................. C12P 19/34; C12Q 1/68; G01N 33/00; C07H 21/02; C07H 21/04
(52) U.S. Cl. ..................... 435/91.2; 435/6; 435/91.1; 435/91.51; 436/94; 536/23.1; 536/24.3; 536/24.33
(58) Field of Search ..................... 435/6, 91.1, 91.2, 435/91.5, 91.51, 183; 436/94; 536/23.1, 24.3, 24.33, 25.3, 25.32

(56) References Cited

U.S. PATENT DOCUMENTS

| 4,200,110 A | 4/1980 | Peterson et al. |
| 4,499,052 A | 2/1985 | Fulwyler |
| 4,682,895 A | 7/1987 | Costello |
| 4,785,814 A | 11/1988 | Kane |

(Continued)

FOREIGN PATENT DOCUMENTS

| EP | 0 269 764 A1 | 6/1988 |
| EP | 0 392 546 A2 | 10/1990 |
| EP | 0 478 319 A1 | 4/1992 |
| EP | 0 723 146 A1 | 7/1996 |
| WO | WO 89/11101 A1 | 11/1989 |
| WO | WO 93/02360 A1 | 2/1993 |
| WO | WO 93/25563 A1 | 12/1993 |
| WO | WO 94/02515 A1 | 2/1994 |
| WO | WO 95/16918 A1 | 6/1995 |

(Continued)

OTHER PUBLICATIONS

Abel et al., "Fiber–Optic Evanescent Wave Biosensor for the Detection of Oligonucleotides," Anal. Chem. 68:2905–2912 (1996).

(Continued)

Primary Examiner—Ethan Whisenant
Assistant Examiner—Frank Wu
(74) Attorney, Agent, or Firm—McDermott, Will & Emery

(57) ABSTRACT

The present invention is directed to sensitive and accurate multiplexed assays for target analyte detection.

34 Claims, 11 Drawing Sheets

U.S. PATENT DOCUMENTS

| | | |
|---|---|---|
| 4,822,746 A | 4/1989 | Walt |
| 4,824,789 A | 4/1989 | Yafuso et al. |
| 4,999,306 A | 3/1991 | Yafuso et al. |
| 5,002,867 A | 3/1991 | Macevicz |
| 5,028,545 A | 7/1991 | Soini |
| 5,105,305 A | 4/1992 | Betzig et al. |
| 5,114,864 A | 5/1992 | Walt |
| 5,132,242 A | 7/1992 | Cheung |
| 5,143,853 A | 9/1992 | Walt |
| 5,194,300 A | 3/1993 | Cheung |
| 5,244,636 A | 9/1993 | Walt et al. |
| 5,244,813 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,298,741 A | 3/1994 | Walt et al. |
| 5,302,509 A | 4/1994 | Cheeseman |
| 5,320,814 A | 6/1994 | Walt et al. |
| 5,357,590 A | 10/1994 | Auracher |
| 5,380,489 A | 1/1995 | Sutton et al. |
| 5,435,724 A | 7/1995 | Goodman et al. |
| 5,474,895 A | 12/1995 | Ishii et al. |
| 5,481,629 A | 1/1996 | Tabuchi |
| 5,494,798 A | 2/1996 | Gerdt et al. |
| 5,494,810 A | 2/1996 | Barany et al. |
| 5,496,997 A | 3/1996 | Pope |
| 5,512,490 A | 4/1996 | Walt et al. |
| 5,516,635 A | 5/1996 | Ekins et al. |
| 5,541,311 A | 7/1996 | Dahlberg et al. |
| 5,554,516 A | 9/1996 | Kacian et al. |
| 5,565,324 A | 10/1996 | Still et al. |
| 5,573,909 A | 11/1996 | Singer et al. |
| 5,575,849 A | 11/1996 | Honda et al. |
| 5,604,097 A | 2/1997 | Brenner |
| 5,632,957 A | 5/1997 | Heller et al. |
| 5,633,972 A | 5/1997 | Walt et al. |
| 5,639,603 A | 6/1997 | Dower et al. |
| 5,656,241 A | 8/1997 | Seifert et al. |
| 5,660,988 A | 8/1997 | Duck et al. |
| 5,679,524 A | 10/1997 | Nikiforov et al. |
| 5,690,894 A | 11/1997 | Pinkel et al. |
| 5,763,175 A | 6/1998 | Brenner |
| 5,780,231 A | 7/1998 | Brenner |
| 5,795,714 A | 8/1998 | Cantor et al. |
| 5,814,524 A | 9/1998 | Walt |
| 5,830,711 A | 11/1998 | Barany et al. |
| 5,840,256 A | 11/1998 | Demers et al. |
| 5,854,033 A | 12/1998 | Lizardi |
| 5,854,684 A | 12/1998 | Stabile et al. |
| 5,856,083 A | 1/1999 | Chelsky et al. |
| 5,858,732 A | 1/1999 | Solomon et al. |
| 5,863,708 A | 1/1999 | Zanzucchi et al. |
| 5,888,723 A | 3/1999 | Sutton et al. |
| 5,900,481 A | 5/1999 | Lough et al. |
| 5,976,797 A | 11/1999 | Mitsuhashi |
| 6,013,456 A | 1/2000 | Akgavan-Tafti |
| 6,023,540 A | 2/2000 | Walt et al. |
| 6,027,889 A | 2/2000 | Barany et al. |
| 6,051,380 A | 4/2000 | Sosnowski et al. |
| 6,054,564 A | 4/2000 | Barany et al. |
| 6,083,763 A | 7/2000 | Balch |
| 6,110,678 A | 8/2000 | Weisburg et al. |
| 6,172,218 B1 | 1/2001 | Brenner |
| 6,251,639 B1 | 6/2001 | Kurn |
| 6,268,148 B1 | 7/2001 | Barany et al. |
| 6,274,323 B1 | 8/2001 | Bruchez et al. |
| 6,306,643 B1 | 10/2001 | Gentalen et al. |
| 6,355,431 B1 | 3/2002 | Chee et al. |

FOREIGN PATENT DOCUMENTS

| | | |
|---|---|---|
| WO | WO 95/21271 A1 | 8/1995 |
| WO | WO 96/03212 A1 | 2/1996 |
| WO | WO 96/15271 A1 | 5/1996 |
| WO | WO 96/30392 A1 | 10/1996 |
| WO | WO 97/14028 A2 | 4/1997 |
| WO | WO 97/31256 A2 | 8/1997 |
| WO | WO 97/14928 A1 | 10/1997 |
| WO | WO 97/40385 A1 | 10/1997 |
| WO | WO 97/45559 A1 | 12/1997 |
| WO | WO 97/46704 A1 | 12/1997 |
| WO | WO 98/04746 A1 | 2/1998 |
| WO | WO 98/13523 A1 | 4/1998 |
| WO | WO 98/31836 A1 | 7/1998 |
| WO | WO 98/40726 A1 | 9/1998 |
| WO | WO 98/50782 A3 | 11/1998 |
| WO | WO 98/53093 A1 | 11/1998 |
| WO | WO 98/53300 A2 | 11/1998 |
| WO | WO 99/18434 A1 | 4/1999 |
| WO | WO 99/39001 A2 | 8/1999 |
| WO | WO 99/60170 A1 | 11/1999 |
| WO | WO 99/67414 A1 | 11/1999 |
| WO | WO 99/64867 A1 | 12/1999 |
| WO | WO 99/67641 A2 | 12/1999 |
| WO | WO 00/04372 A1 | 1/2000 |
| WO | WO 00/13004 A2 | 3/2000 |
| WO | WO 00/16101 A2 | 3/2000 |
| WO | WO 00/39587 A1 | 7/2000 |
| WO | WO 00/47996 A2 | 8/2000 |
| WO | WO 00/48000 A1 | 9/2000 |
| WO | WO 00/58516 A2 | 10/2000 |
| WO | WO 00/63437 A2 | 10/2000 |
| WO | WO 00/71243 A1 | 11/2000 |
| WO | WO 00/71992 A1 | 11/2000 |
| WO | WO 00/71995 A2 | 11/2000 |
| WO | WO 00/75373 A2 | 12/2000 |

OTHER PUBLICATIONS

Anonymous, "Microsphere Selection Guide," Bandg Laboratories, (Fisher, In) Sep. 1998.

Anonymous, "Fluorescent Microspheres," Tech. Note 19, Bang Laboratories, (Fishers, In) Feb. 1997.

Bangs, L.B., "Immunological Applications of Microspheres," The Latex Course, Bangs Laboratories (Carmel, IN) Apr. 1996.

Barnard et al., "A Fiber–Optic Chemical Sensor with Discrete Sensing Sites," Nature, 353:338–340 (Sep. 1991).

Chen et al., "A Microsphere–Based Assay for Multiplexed Single Nucleotide Polymorphism Analysis Using Single Base Chain Extension," Genome Research, 10(4):549–557 (2000).

Czarnik, "Illuminating the SNP Genomic Code," Modern Drug Discovery, 1(2): 49–55 (1998).

Drmanac, R. et al., "Sequencing by Oligonucleotide Hybridization: A Promising Framework in Decoding of the Genome Program," The First International Conference on Electrophoresis, Supercomputing and the Human Genome, Proceeding os th Apr. 10–13, 1990 Conference at Florida State University. Ed. C. Cantor and H. Lim.

Drmanac, R. et al., "Prospects for a Miniaturized, Simplified and Frugal Human Genome Project," Scientia Yugoslavica, 16(1–2):97–107 (1990).

Drmanac, R. et al., "Sequencing by Hybridization (SBH) with Oligonucleotide Probes as an Integral Approach for the Analysis of Complex Genomes," International Journal of Genome Research, 1(1):59–79 (1992).

Drmanac, R. et al., "Sequencing by Hybridization," Automated DNA Sequencing and Analysis, ed. M. Adams, C. Fields and J. Venter. (1994).

Ferguson et al., "A Fiber–Optic DNA Biosensor Microarray for the Analysis of Gene Expression," Nature Biotechnology, 14:1681–1684 (1996).

Fuh et al., "Single Fibre Optic Fluorescence pH Probe," Analyst, 112:1159–1163 (1987).

Healey et al., "Improved Fiber–Optic Chemical Sensor for Penicillin," Anal. Chem. 67(24):4471–4476 (1995).

Healey et al., "Development of a Penicillin Biosensor Using a Single Optical Imaging Fiber," SPIE Proc. 2388:568–573 (1995).

Healey et al., "Fiberoptic DNA Sensor Array Capable of Detecting Point Mutations," Analytical Biochemistry, 251:270–279 (1997).

Hirschfeld et al., "Laser–Fiber–Optic "Optrode" for Real Time In Vivo Blood Carbon Dioxide Level Monitoring," Journal of Lightwave Technology, LT–5(7):1027–1033 (1987).

Iannone et al., "Multiplexed Single Nucleotide Polymorphism Genotyping by Oligonucleotide Ligation and Flow Cytometry," Cytometry, 39:131–140 (2000).

Michael et al., "Making Sensors out of Disarray: Optical Sensor Microarrays," Proc. SPIE, 3270: 34–41 (1998).

Michael et al., "Randomly Ordered Addressable High–Density Optical Sensor Arrays," Anal. Chem. 70(7): 1242–1248 (Apr. 1998).

Michael et al., "Fabrication of Micro– and Nanostructures Using Optical Imaging Fibers and there Use as Chemical Sensors," Proc. 3rd Intl. Symp., Microstructures and Microfabricated Systems, ed. P.J. Hesketh, et al., v. 97–5, Electrochem. Soc., 152–157 (Aug. 1997).

Mignani, et al., "In–Vivo Biomedical Monitoring by Fiber–Optic Systems," Journal of Lightwave Technology, 13(7): 1396–1406 (1995).

Pantano et al., "Ordered Nanowell Arrays," Chem. Mater., 8(12): 2832–2835 (1996).

Peterson et al., "Fiber–Optic Sensors for Biomedical Applications," Science, 13:123–127 (1984).

Peterson, J. et al., "Fiber–Optic pH Probe for Physiological Use," Anal. Chem., 52:864–869 (1980).

Piunno et al., "Fiber–Optic DNA Sensor for Fluorometric Nucleic Acid Determination," Anal. Chem., 67:2635–2643 (1995).

Pope, E. "Fiber Optic Chemical Microsensors Employing Optically Active Silica Microspehres," SPIE, 2388:245–256 (1995).

Strachan et al., "A Rapid General Method for the Identification of PCR Products Using a Fibre–Optic Biosensor and its Application to the Detection of Listeria," Letters in Applied Microbiology, 21:5–9 (1995).

Walt, D. "Fiber Optic Imaging Sensors," Accounts of Chemical Research, 31(5):267–278 (1998).

Walt, "Fiber–Optic Sensors for Continuous Clinical Monitoring," Proc. IEEE, 80(6): 903–911 (1992).

Lyamichev et al., "Polymorphism identification and quantitative detection of genomic DNA by invasive cleavage of oligonucleotide probes," Nature Biotechnology, 17:292–296 (1999).

Shoemaker et al., "Quantitative phenotypic analysis of yeast deletion mutants using a highly parallel molecular bar–coding strategy," Nature Genetics, 14:450–456 (1996). (A, AS, NA) added Aug. 1, 2001.

Metzker et al., "Termination of DNA synthesis by novel 3'–modified–deoxyribonucleoside 5'–triphosphates," Nucleic Acids Research, 22(20):4259–4267 (1994).

Baner et al., "Signal Amplification of Patlock Probes by Rolling Circle Replication," Nucleic Acids Research, 26(22), pp. 5073–5078, 1998.

Lizardi et al., "Mutation Detection and Single–Molecule Counting Using Isothermal Rolling–Circle Amplification," Nature genetics, 19, pp. 225–232, Jul. 1998.

Ronaghi et al., "A Sequencing Method Based on Real–Time Pyrophosphate," Science, 281, pp. 363–365, 1998.

Syvanen, A., "From gels to chips: "Minisequencing" PrimerExtension for Analysis of Point Mutations and Single Nucleotide Polymorphisms," Human Mutation, 13, pp. 1–10, 1999.

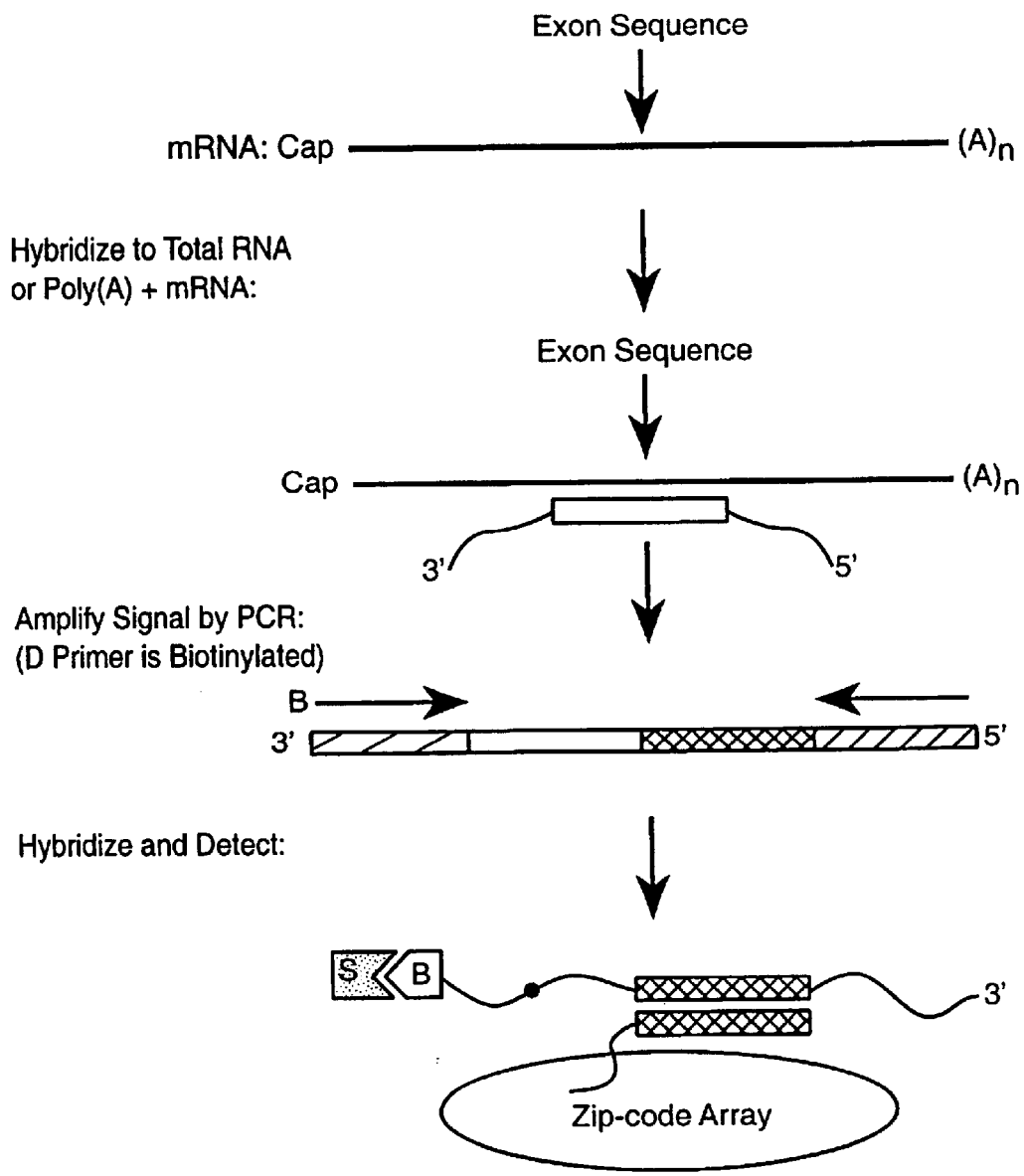
FIG._1

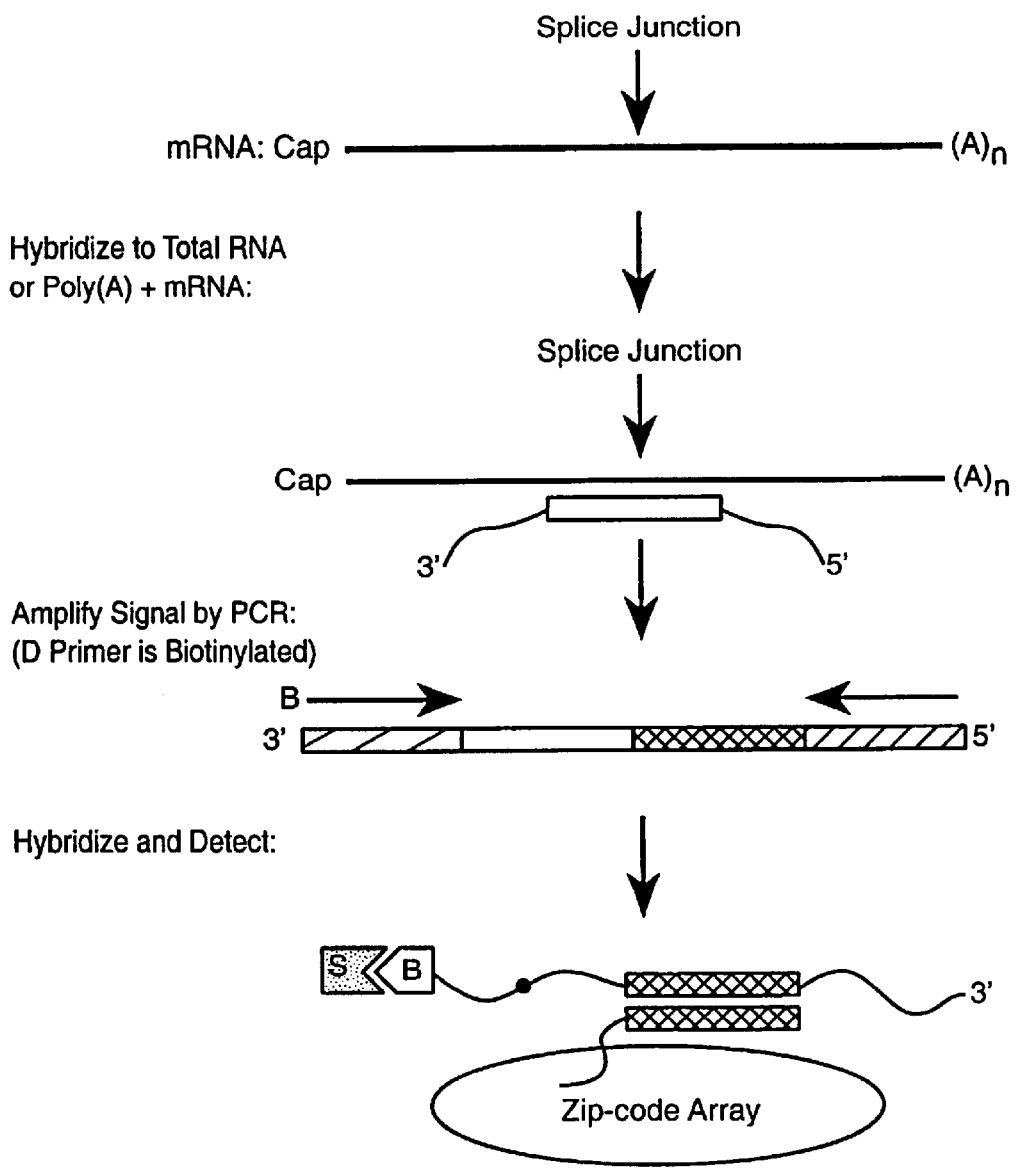
FIG._2

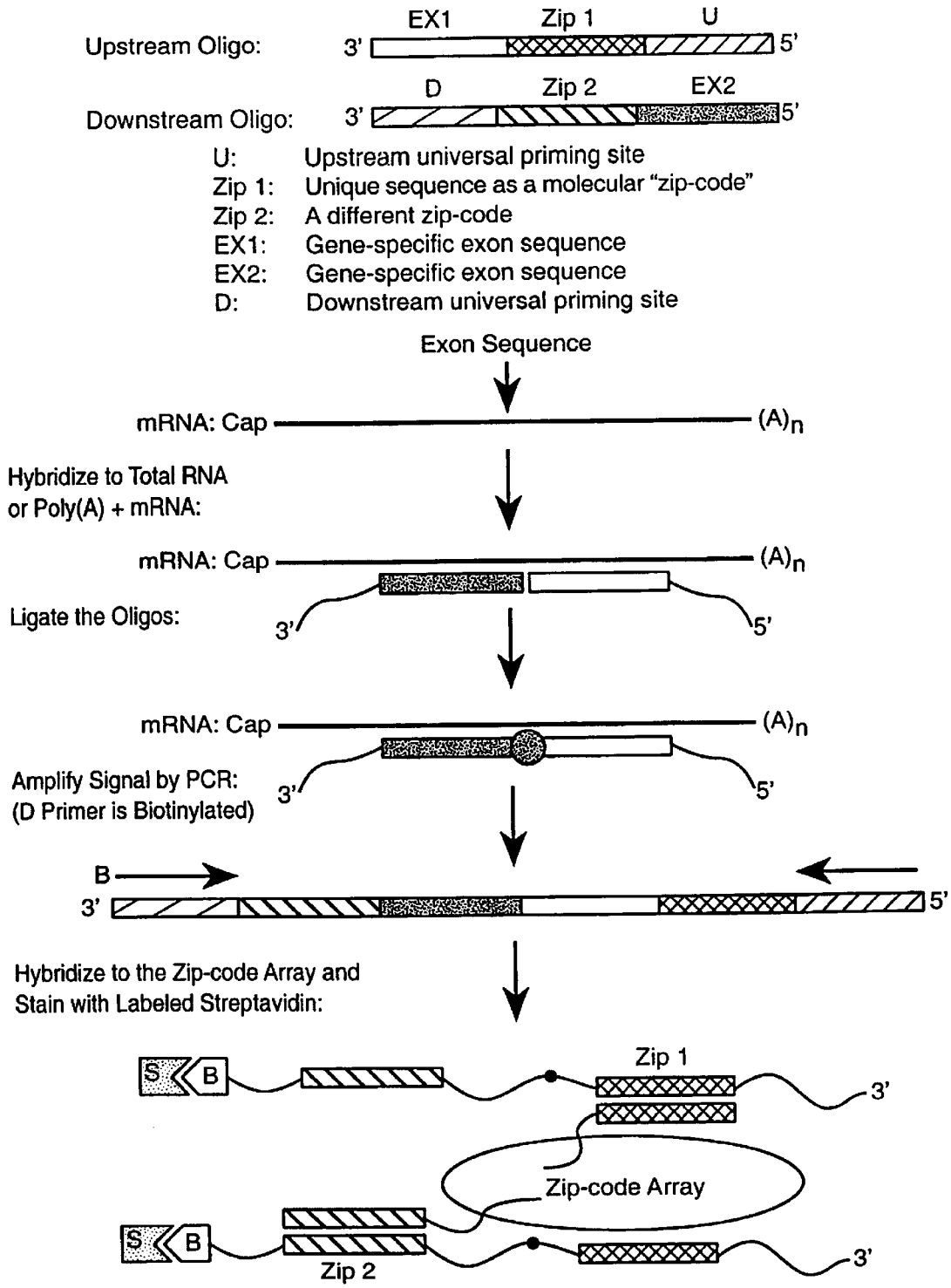
FIG._3

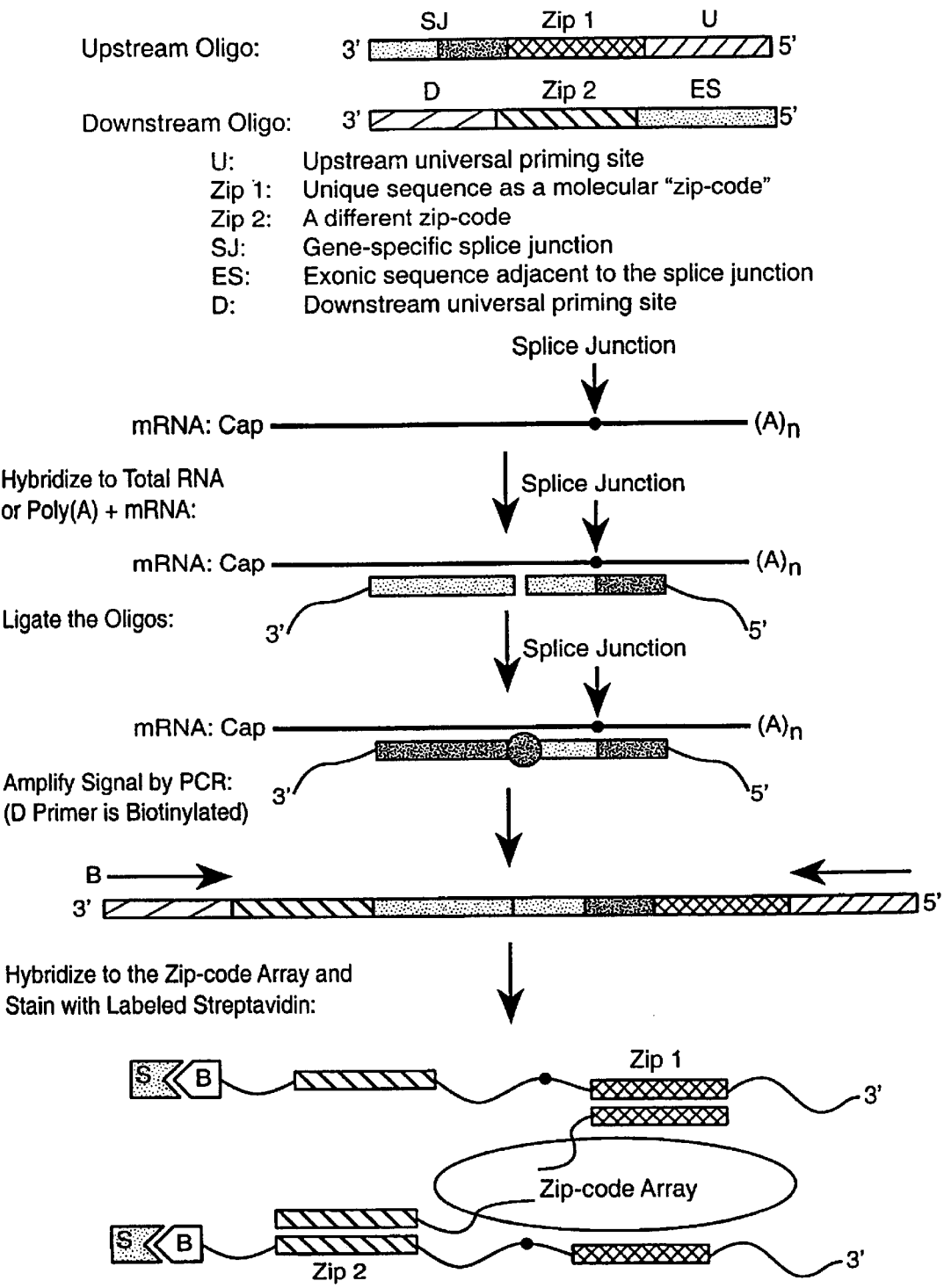
FIG._4

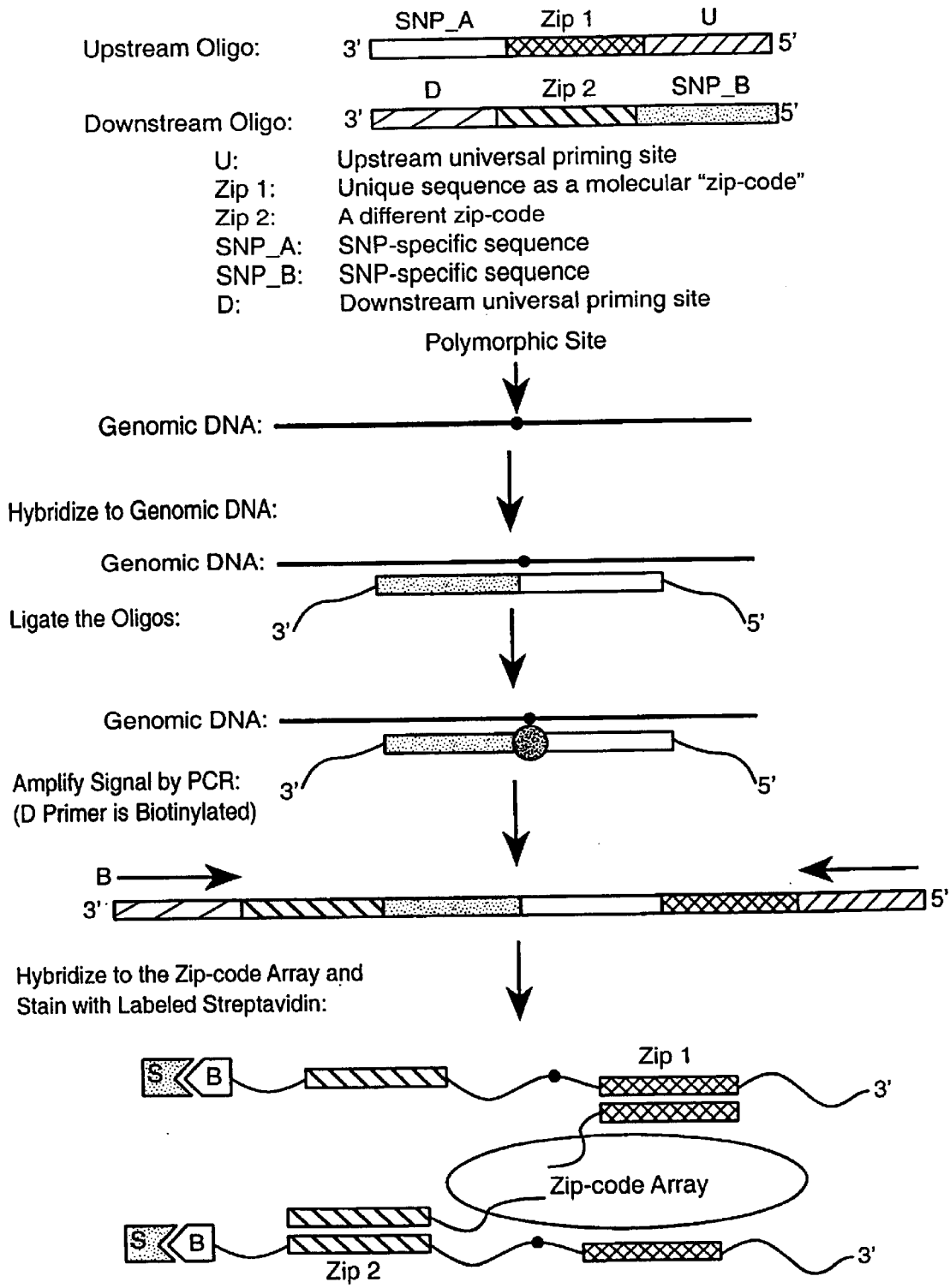
FIG._5

FIG._6

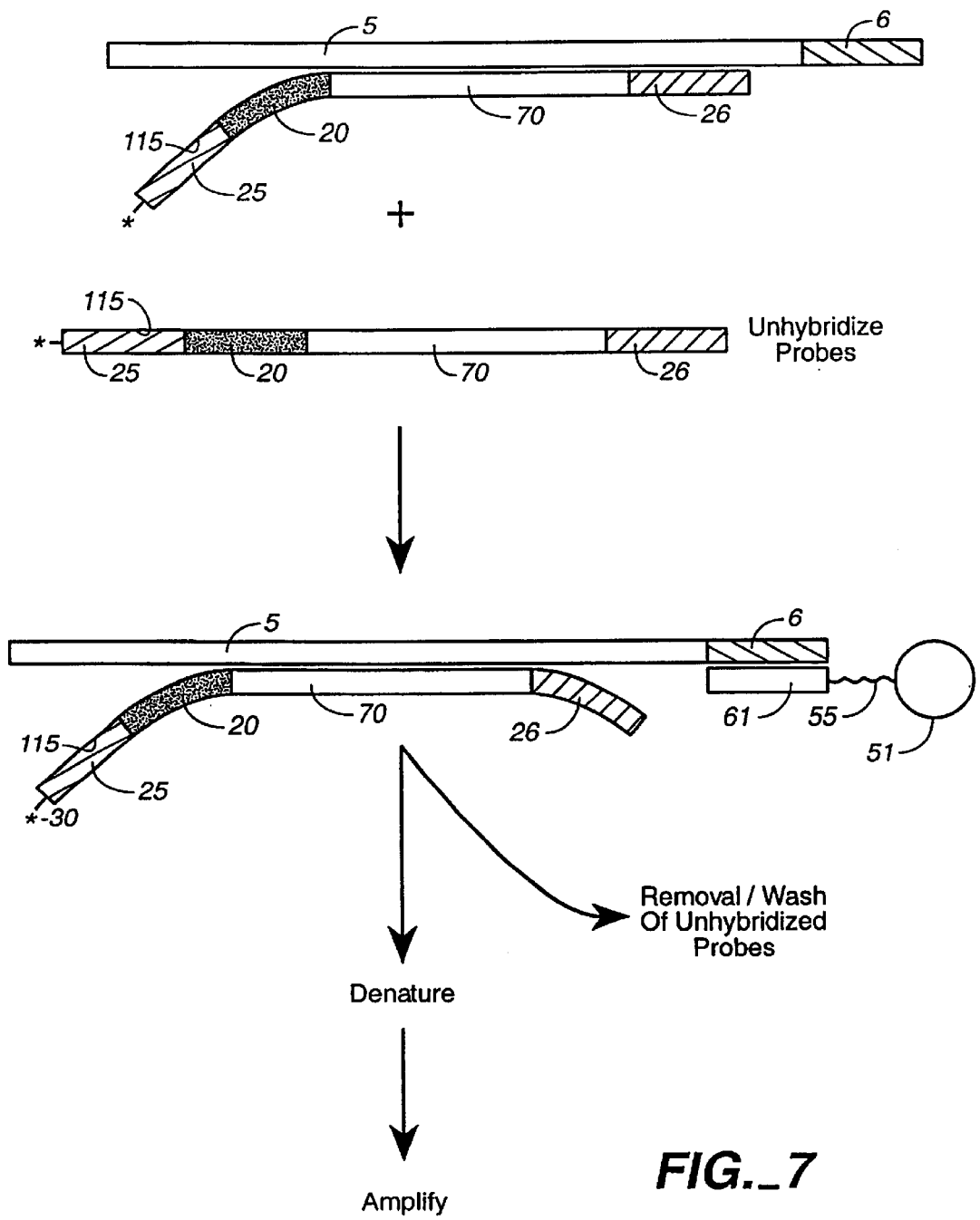
FIG._7

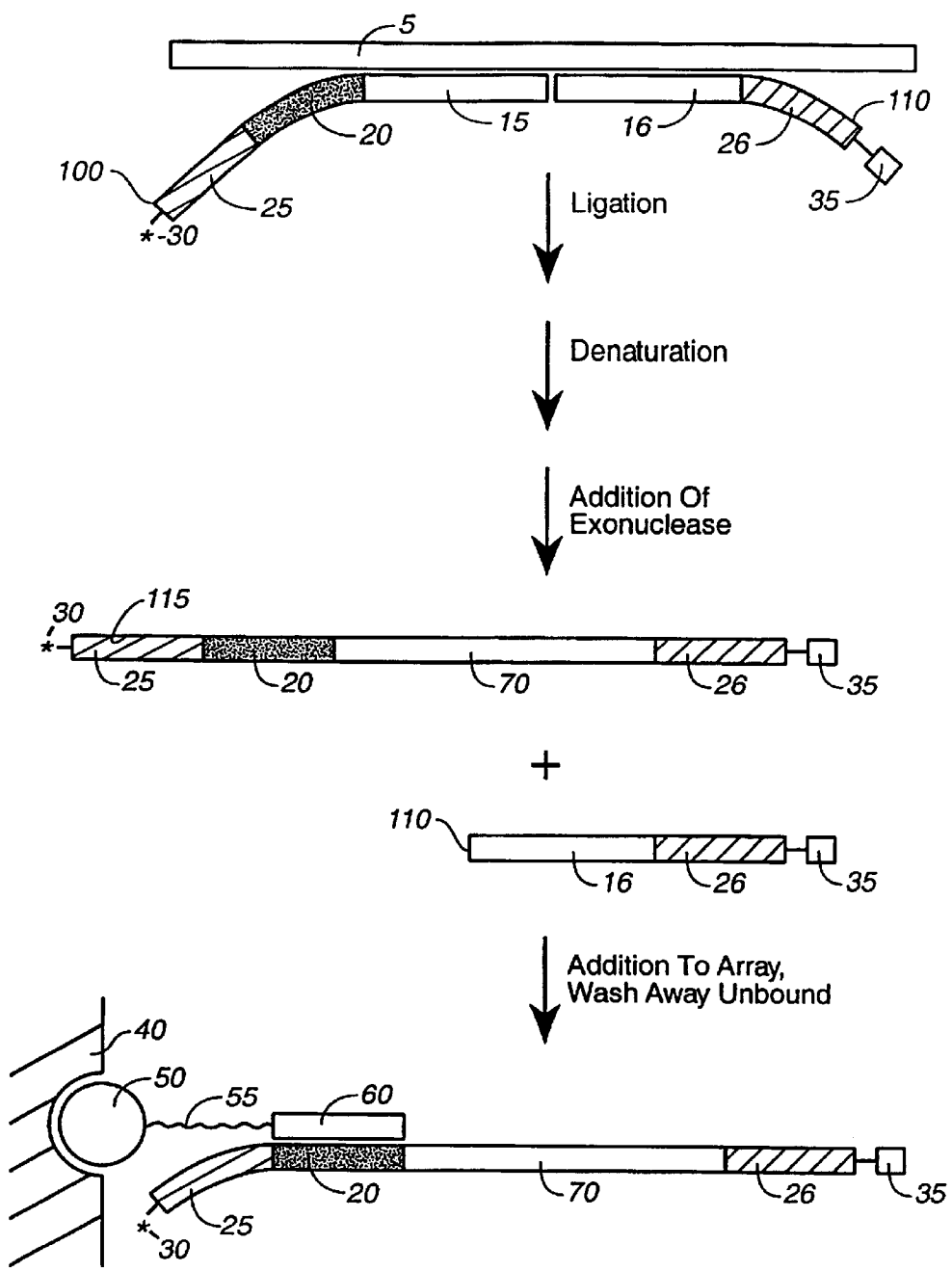
FIG._8

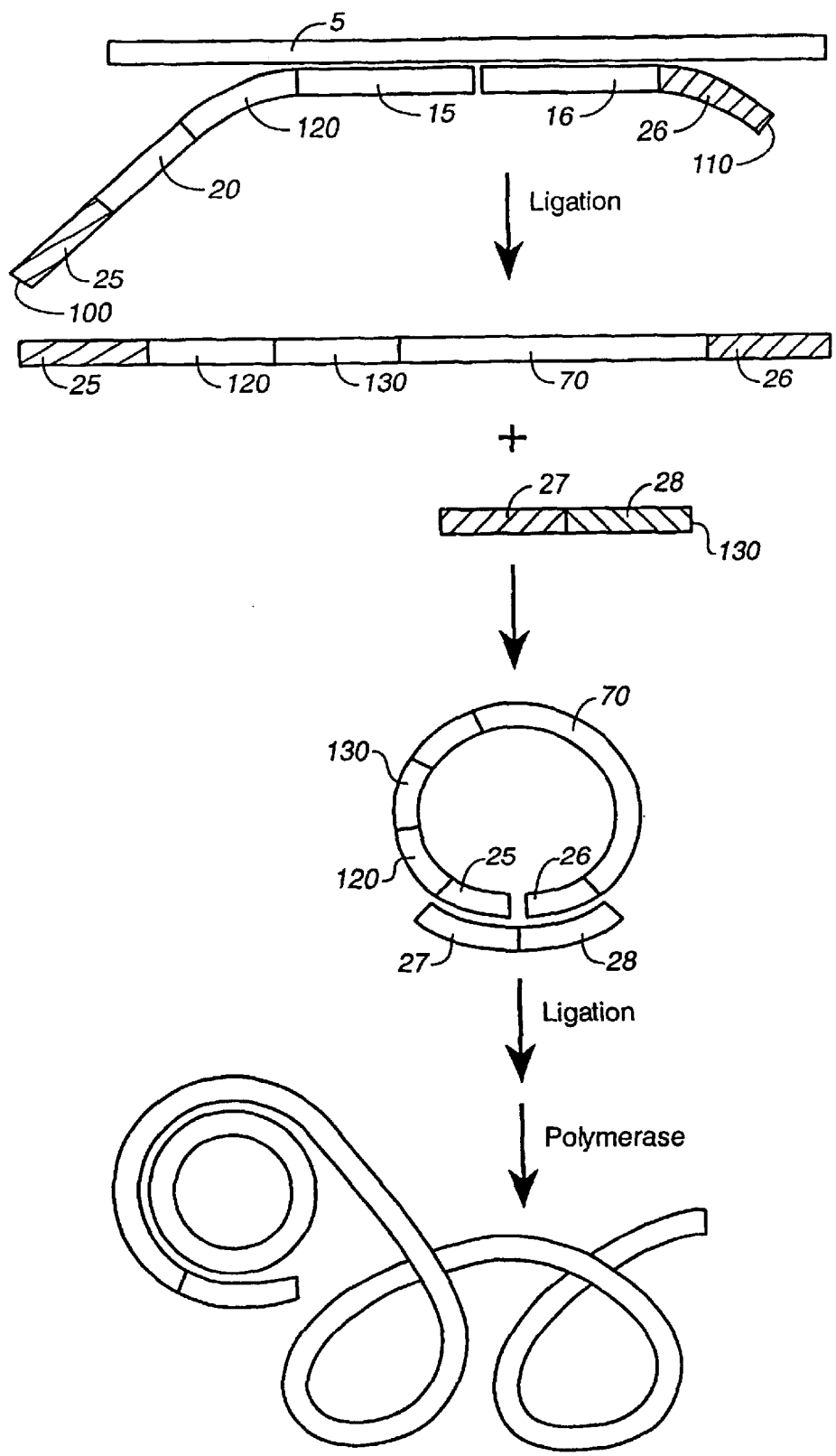
FIG._9

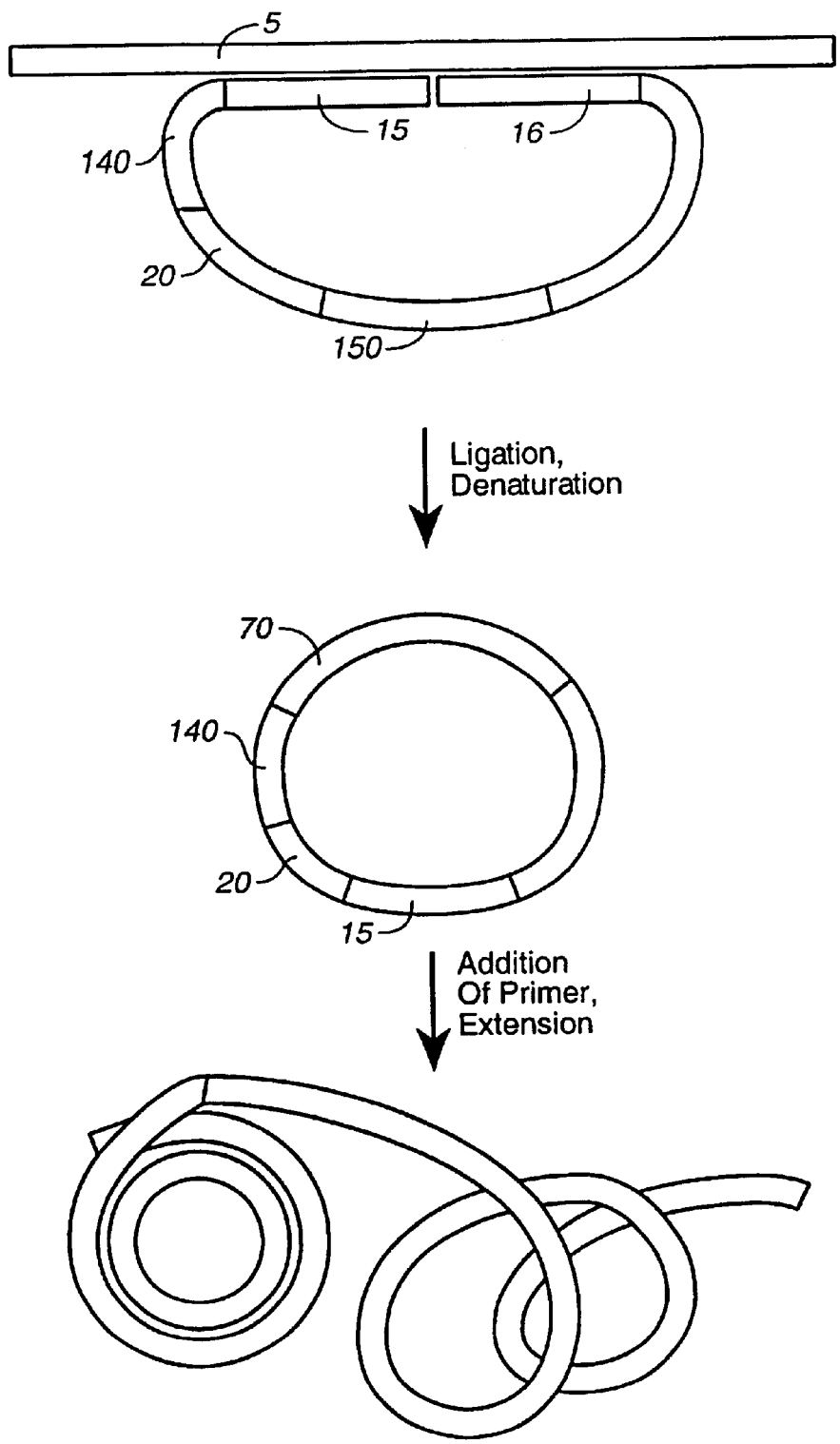
FIG._10

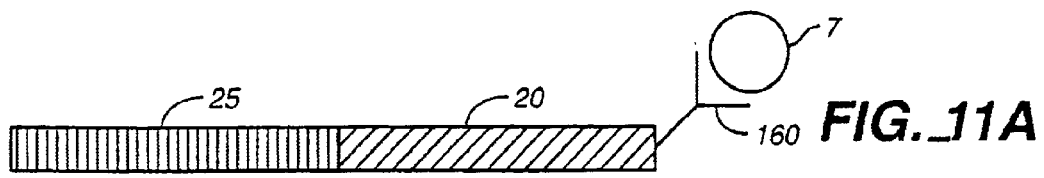
FIG._11A
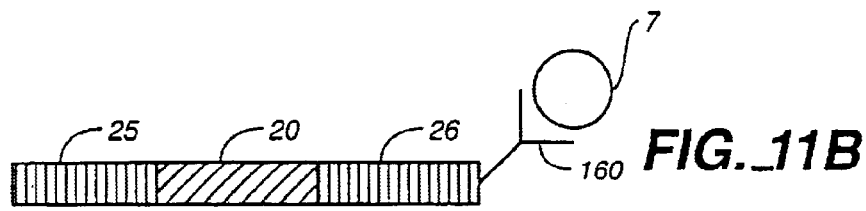
FIG._11B
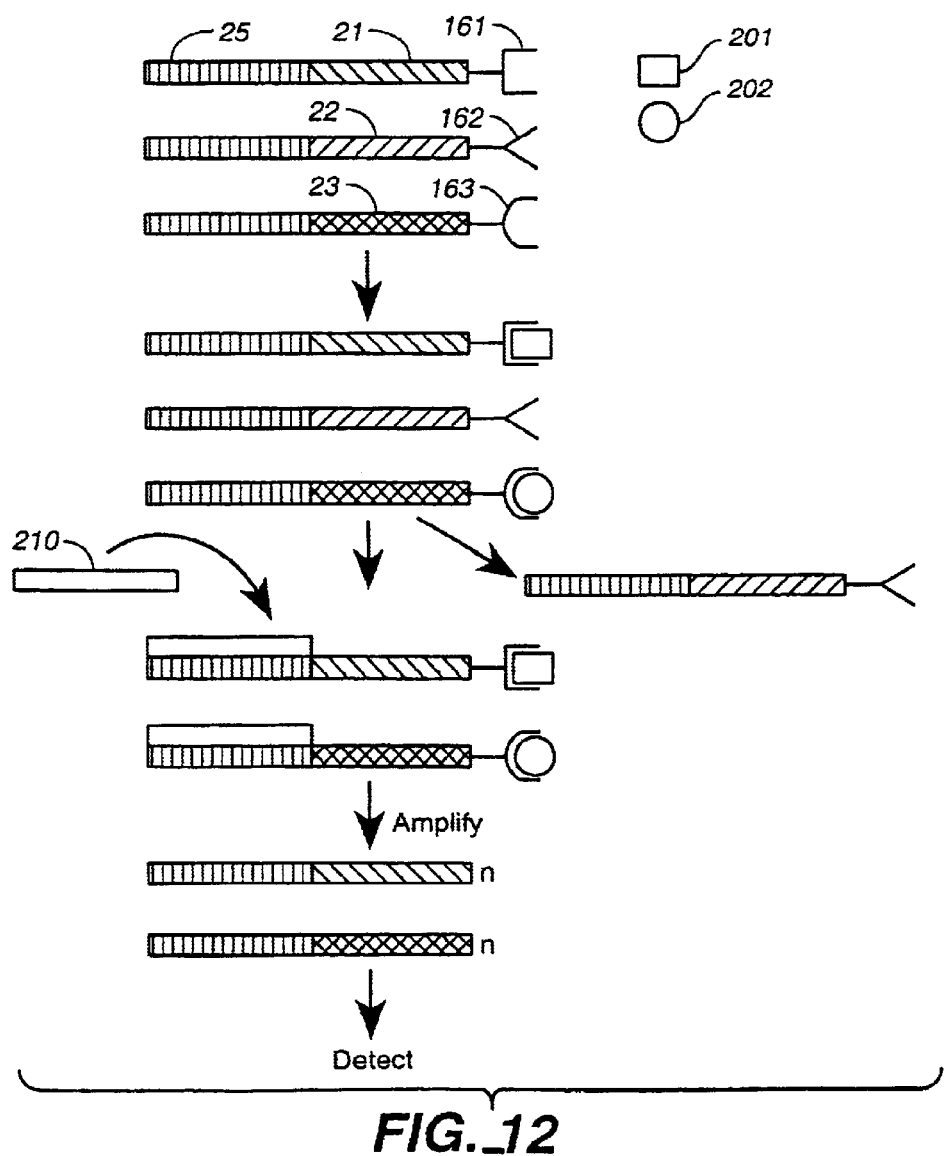
FIG._12

MULTIPLEXED DETECTION OF ANALYTES

The present application claims the benefit of application U.S. Ser. No. 60/297,609, filed Jun. 11, 2001, Ser. No. 60/180,810, filed Feb. 7, 2000 and No. 60/234,143, filed Sep. 21, 2000, and is a continuing application of Ser. No. 09/779,376, filed Feb. 7, 2001, all of which are expressly incorporated herein by reference.

FIELD OF THE INVENTION

The present invention is directed to sensitive and accurate multiplexed assays for target analyte detection.

BACKGROUND OF THE INVENTION

The detection of various target analytes or molecules is an important tool for a variety of application including diagnostic medicine, molecular biology research and detection of contaminants, to name a few. While method of detecting different analytes has evolved, the ability to detect numerous target analytes simultaneously has proven difficult. Detection of multiple proteins, for example has been limited to conventional electrophoresis assays or immunoassays. There has not been a significant multiplexed protein detection assay or method.

The detection of specific nucleic acids is an important tool for diagnostic medicine and molecular biology research. Gene probe assays currently play roles in identifying infectious organisms such as bacteria and viruses, in probing the expression of normal and mutant genes and identifying mutant genes such as oncogenes, in typing tissue for compatibility preceding tissue transplantation, in matching tissue or blood samples for forensic medicine, and for exploring homology among genes from different species.

Ideally, a gene probe assay should be sensitive, specific and easily automatable (for a review, see Nickerson, Current Opinion in Biotechnology 4:48–51 (1993)). The requirement for sensitivity (i.e. low detection limits) has been greatly alleviated by the development of the polymerase chain reaction (PCR) and other amplification technologies which allow researchers to amplify exponentially a specific nucleic acid sequence before analysis (for a review, see Abramson et al., Current Opinion in Biotechnology, 4:41–47 (1993)).

Specificity, in contrast, remains a problem in many currently available gene probe assays. The extent of molecular complementarity between probe and target defines the specificity of the interaction. Variations in the concentrations of probes, of targets and of salts in the hybridization medium, in the reaction temperature, and in the length of the probe may alter or influence the specificity of the probe/target interaction.

It may be possible under some circumstances to distinguish targets with perfect complementarity from targets with mismatches, although this is generally very difficult using traditional technology, since small variations in the reaction conditions will alter the hybridization. New experimental techniques for mismatch detection with standard probes include DNA ligation assays where single point mismatches prevent ligation and probe digestion assays in which mismatches create sites for probe cleavage.

Recent focus has been on the analysis of the relationship between genetic variation and phenotype by making use of polymorphic DNA markers. Previous work utilized short tandem repeats (STRs) as polymorphic positional markers; however, recent focus is on the use of single nucleotide polymorphisms (SNPs), which occur at an average frequency of more than 1 per kilobase in human genomic DNA. Some SNPs, particularly those in and around coding sequences, are likely to be the direct cause of therapeutically relevant phenotypic variants and/or disease predisposition. There are a number of well known polymorphisms that cause clinically important phenotypes; for example, the apoE2/3/4 variants are associated with different relative risk of Alzheimer's and other diseases (see Cordor et al., Science 261(1993). Multiplex PCR amplification of SNP loci with subsequent hybridization to oligonucleotide arrays has been shown to be an accurate and reliable method of simultaneously genotyping at least hundreds of SNPs; see Wang et al., Science, 280:1077 (1998); see also Schafer et al., Nature Biotechnology 16:33–39 (1998). However, in Wang et al. only 50% of 558 SNPs were amplified successfully in a single multiplexed amplification reaction. As such, there exists a need for methods that increase the fidelity and robustness of multiplexing assays.

Accordingly, highly multiplexed detection or genotyping of nucleic acid sequences is desirable to permit a new scale of genetic analysis. Simultaneously detecting many hundreds, to multiple thousands of nucleic acid sequences, will require methods which are sensitive and specific despite high background complexity. In order for such reactions to be conducted at low cost to permit widespread use of such techniques, uniform sample preparation and reaction conditions must be applied, preferably in an automatable fashion. A variety of various nucleic acid reaction schemes, amplification techniques, and detection platforms have been used in the past toward this end goal, but none have been able to robustly achieve sensitive, accurate levels of multiplexing beyond a few hundred loci.

Accordingly, it is an object of the invention to provide a very sensitive and accurate multiplexed approach for nucleic acid detection with uniform sample preparation and reaction conditions.

BRIEF DESCRIPTION OF THE DRAWINGS

FIG. 1 depicts a flow chart for array based detection of gene expression.

FIG. 2 depicts a flow chart for array-based detection of RNA Alternative Splicing.

FIG. 3 depicts a flow chart for genome-wide expression profiling using oligonucleotide-ligation strategy.

FIG. 4 depicts a flow chart for genome-wide RNA alternative splicing monitoring using oligonucleotide-ligation strategy.

FIG. 5 depicts a flow chart for direct genotyping using a whole-genome oligonucleotide-ligation strategy.

FIG. 6 depicts a flow chart for whole-genome oligonucleotide-ligation strategy.

FIG. 7 depicts a preferred embodiment of the invention utilizing a poly(A)-poly(T) capture to remove unhybridized probes and targets. Target sequence 5 comprising a poly(A) sequence 6 is hybridized to target probe 115 comprising a target specific sequence 70, an adapter sequence 20, an upstream universal priming site 25, a downstream universal priming site 26 and an optional label 30. The resulting hybridization complex is contacted with a bead 51 comprising a linker 55 and a poly(T) capture probe 61.

FIG. 8 depicts a preferred embodiment of removing non-hybridized target probes, utilizing an OLA format. Target 5 is hybridized to a first ligation probe 100 comprising a first target specific sequence 15, an adapter sequence 20, an upstream universal priming site 25, and an optional label 30, and a second ligation probe 110 comprising a second target specific sequence 16, a downstream universal priming site 26, and a nuclease inhibitor 35. After ligation, denaturation of the hybridization complex and addition of an exonuclease, the ligated target probe 115 and the second ligation probe 110 is all that is left. The addition of this to an array (in this embodiment, a bead array comprising substrate 40, bead 50 with linker 55 and capture probe 60 that is substantially complementary to the adapter sequence 20), followed by washing away of the second ligation probe 110 results in a detectable complex.

FIG. 9 depicts a preferred rolling circle embodiment utilizing two ligation probes. Target 5 is hybridized to a first ligation probe 100 comprising a first target specific sequence 15, an adapter sequence 20, an upstream universal priming site 25, an adapter sequence 20 and a RCA primer sequence 120, and a second ligation probe 110 comprising a second target specific sequence 16 and a downstream universal priming site 26. Following ligation, an RCA sequence 130 is added, comprising a first universal primer 27 and a second universal primer 28. The priming sites hybridize to the primers and ligation occurs, forming a circular probe. The RCA sequence 130 serves as the RCA primer for subsequent amplification. An optional restriction endonuclease site is not shown.

FIG. 10 depicts preferred a rolling circle embodiment utilizing a single target probe. Target 5 is hybridized to a target probe 115 comprising a first target specific sequence 15, an adapter sequence 20, a RCA priming site 140, optional label sequence 150 and a second target specific sequence 16. Following ligation, denaturation, and the addition of the RCA primer and extension by a polymerase, amplicons are generated. An optional restriction endonuclease site is not shown.

FIG. 11 depicts two configurations of probes for multiplex detection of analytes. A depicts a probe containing an adapter 20, an upstream priming site 25 and a target-specific portion, i.e. bioactive agent 160 bound to a target analyte 7. B depicts a probe containing an adapter 20, an upstream universal priming site 25, a downstream universal priming site 26 and a target-specific portion, i.e. bioactive agent 160 bound to a target analyte 7.

FIG. 12 depicts a preferred method for multiplex detection of analytes. Probes containing universal priming sequence 25 and adapters that identify the target analyte to be detected 21, 22 and 23, and target specific portions, i.e. bioactive agents 161, 162 and 163 are contacted with target analytes 201 and 202. Probes to which target analytes bind are contacted with universal primers 210 and amplification reaction mixture. Amplicons are detected and serve as an indication of the presence of the target analyte.

SUMMARY OF THE INVENTION

In accordance with the embodiments outlined above, the present invention permits highly multiplexed detection of target analytes. The method includes contacting target analytes with a composition comprising an amplification enzyme and first and second target probes. The first and second target probes comprising a first and second bioactive agent, respectively, that specifically bind to the first and second target molecules. The probes also comprise a first and second adapter sequence, respectively, such that the first adapter sequence identifies the first target molecule and the second adapter sequence identifies the second target molecule, and at least a first and second upstream universal priming sequence, respectively. The first and second adapter sequences, wherein no ligation is performed, to form first and second amplicons, respectively, and detecting the first and second amplicons, whereby the first and second target molecules, respectively, are detected.

In addition, the invention provides a method for multiplex detection of a plurality of target molecules comprising contacting a plurality of target molecules with a composition comprising an amplification enzyme and a plurality of target probes, each comprising a bioactive agent, wherein the bioactive agent binds to discrete target molecules an adapter sequence that identifies the discrete target molecule that binds the bioactive agent and at least a first upstream universal primer, amplifying the adapter sequences, wherein no ligation is performed, to form a plurality of amplicons, and detecting the plurality of amplicons, whereby the plurality of target molecules, are detected.

In addition, present invention permits highly multiplexed nucleic acid detection reactions under uniform sample preparation and reaction conditions. That is, preferably the method includes multiplexing from hundreds to thousands of assays simultaneously, more preferably up to tens of thousands of assays simultaneously, most preferably up to millions of assays. The inventive method preferably includes 1) immobilizing the sample nucleic acids to be interrogated (in a preferred embodiment, genomic DNA) on a capture surface, such as a solid phase (in a preferred embodiment, immobilizing the genomic DNA on beads); 2) simultaneously conducting at least a first step of a nucleic acid detection reaction with the captured nucleic acids (in the preferred embodiment, the nucleic acid detection reaction comprises two phases: the first phase involves the exposure of the sample nucleic acids to a set of sequence-specific probe(s), the second phase involves an enzymatic step to assure specificity of the nucleic acid detection reaction. The probes used include at least one appropriate universal amplification priming site); 3) a stringent wash step to reduce the complexity of the multiplexed probe mixture by washing away unhybridized probes; 4) optionally conducting the second phase of the nucleic acid detection reaction step of 2) above (in the case of for example competitive hybridization as the nucleic acid detection reaction, no second phase is required); 5) releasing the probes from the sample nucleic acid; 6) amplification of the released probes (exponential or linear amplification schemes such as PCR, or Invader™, ESPIA (see WO 01/20035, which is expressly incorporated herein by reference), T7 amplification or the novel amplification method disclosed in Application patent application filed Jul. 12, 2001, entitled METHODS OF MULTIPLEXING AMPLIFICATION AND GENOTYPING REACTIONS (no serial number received)) using the universal amplification priming site(s) on the probes; and 6) detection and readout of the amplified signals on any detection platform (in a preferred embodiment, the randomly assembled BeadArray™ technology platform).

DETAILED DESCRIPTION OF THE INVENTION

The present invention is directed to the multiplex preparation and detection of target analytes. In general, the invention involves the use of probes that comprise a number of components. First of all, the probes comprise a bioactive agent (e.g. one of a binding partner pair) that will bind to all or a portion of the target analyte. This bioactive agent may comprise nucleic acid, for example when the target analyte is a target nucleic acid sequence, or, when the target analyte is a protein, for example, the bioactive agent may be nucleic acid (sometimes referred to as an aptamer) or a binding partner such as an antibody or ligand.

The probes further comprise at least one adapter nucleic acid sequence that uniquely identifies the target analyte. That is, there is a unique adapter sequence/target analyte pair for each unique target analyte, although in some cases, adapter sequences may be reused.

In addition, the probes also comprise at least one universal nucleic acid priming sequence that will allow the amplification of the adapter sequence. In some cases, one universal priming sequence can be used, for example when the priming sequence comprises an RNA polymerase priming sequence such as a T7 site. Alternatively, two universal priming sequences can be used, such as standard PCR priming sequences, as long as they flank the adapter sequence, e.g. one priming sequence is 5' to the adapter sequence and one is 3'.

Once the probes have been added to the target analytes to form assay complexes (sometimes referred to herein as hybridization complexes when the target analytes are nucleic acids) generally the unhybridized probes are washed away, using a variety of techniques as outlined herein.

In one embodiment the single nucleotide polymorphisms are detected as outlined herein. This analysis step is followed by amplification as described below.

Amplification proceeds in a number of ways. In general, when an RNA polymerase priming sequence is used such as a T7 site, the RNA polymerase is added and copies of the adapter sequence are generated. Alternatively, when the amplification reaction is PCR, two primers are added, each of which is substantially complementary (and preferably perfectly complementary) to one of the universal priming sequences. Again, as outlined more fully below, there may be more than one set of universal priming sequences/primers used in a given reaction. In addition, as will be appreciated by those in the art, a number of other amplification reactions can be done, as outlined below.

The resulting amplicons can be detected in a wide variety of ways, including the use of biochips (e.g. solid support arrays, including both ordered and random arrays, as outlined herein) liquid arrays, mass spectroscopy analysis, etc., in a variety of formats, including sandwich assays.

In some cases, one or more of the target analytes or probes may be attached to a solid support. For example, the target analytes (for example, genomic DNA sequences) can be attached to beads in a variety of ways. The probe pool is added to form assay complexes (sometimes referred to herein as hybridization complexes when the target analytes are nucleic acids) and unhybridized probes are washed away. The probes are denatured off the target analytes, and then amplified as outlined herein.

Alternatively, solution phase assays may be done, followed by either liquid or solid array detection.

Accordingly, the present invention relates to the multiplex amplification and detection of target analytes in a sample. As used herein, the phrase or "multiplex" or grammatical equivalents refers to the detection, analysis or amplification of more than one target analyte of interest. In a one embodiment multiplex refers to at least 100 different target analytes while at least 500 different target analytes is preferred. More preferred is at least 1000, with more than 5000 particularly preferred and more than 10,000 most preferred. Detection is performed on a variety of platforms. In a preferred embodiment the invention is utilized with adapter sequences that identify the target molecule.

Accordingly, the present invention provides compositions and methods for detecting target analytes including detecting and genotyping specific target nucleic acid sequences in a sample and detecting an quantitating proteins. As will be appreciated by those in the art, the sample solution may comprise any number of things, including, but not limited to, bodily fluids (including, but not limited to, blood, urine, serum, lymph, saliva, anal and vaginal secretions, perspiration and semen, of virtually any organism, with mammalian samples being preferred and human samples being particularly preferred). The sample may comprise individual cells, including primary cells (including bacteria), and cell lines, including, but not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells, osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, 923, HeLa, WI-38, Weri-1, MG-63, etc. See the ATCC cell line catalog, hereby expressly incorporated by reference.

If required, the target analyte is prepared using known techniques. For example, the sample may be treated to lyse the cells, using known lysis buffers, sonication, electroporation, etc., with purification and amplification as outlined below occurring as needed, as will be appreciated by those in the art. In addition, the reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents which may be included in the assays. These include reagents like salts, buffers, neutral proteins, e.g. albumin, detergents, etc., which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target.

In addition, when nucleic acids are to be detected preferred methods utilize cutting or shearing techniques to cut the nucleic acid sample containing the target sequence into a size that will facilitate handling and hybridization to the target, particularly for genomic DNA samples. This may be accomplished by shearing the nucleic acid through mechanical forces (e.g. sonication) or by cleaving he nucleic acid using restriction endonucleases.

In addition, in most embodiments, double stranded target nucleic acids are denatured to render them single stranded so as to permit hybridization of the primers and other probes of the invention. A preferred embodiment utilizes a thermal step, generally by raising the temperature of the reaction to about 95° C., although pH changes and other techniques may also be used.

The present invention is directed to methods of detecting target analytes. By "target analyte" or "analyte" or grammatical equivalents herein is meant any molecule, compound or particle to be detected. As outlined below, target analytes preferably bind to binding ligands, as is more fully described herein. As will be appreciated by those in the art, a large number of analytes may be detected using the present methods; basically, any target analyte for which a binding ligand, described herein, may be made may be detected using the methods of the invention.

Suitable analytes include organic and inorganic molecules, including biomolecules. They may include environmental pollutants (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc. Particularly preferred analytes are nucleic acids and proteins (including enzymes, antibodies, antigens, growth factors, cytokines, etc).

In a preferred embodiment, the target analyte is a protein. As will be appreciated by those in the art, there are a large number of possible proteinaceous target analytes that may be detected or evaluated for binding partners using the present invention. Suitable protein target analytes include, but are not limited to, (1) immunoglobulins; (2) enzymes (and other proteins); (3) hormones and cytokines (many of which serve as ligands for cellular receptors); and (4) other proteins. Thus, in one embodiment the method is directed to the detection and/or quantification of protein molecules. In particular, the invention relates to multiplexed detection of proteins. In a preferred embodiment the invention is utilized with adapter sequences that specifically identify the target protein.

In a preferred embodiment, the target analyte is a nucleic acid. By "nucleic acid" or "oligonucleotide" or grammatical equivalents herein means at least two nucleotides covalently linked together. A nucleic acid of the present invention will generally contain phosphodiester bonds, although in some cases, as outlined below, particularly for use with probes or primers, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowski et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp169–176). Several nucleic acid analogs are described in Rawls, C & E News Jun. 2, 1997 page 35. All of these references are hereby expressly incorporated by reference. These modifications of the ribose-phosphate backbone may be done to facilitate the addition of labels, or to increase the stability and half-life of such molecules in physiological environments.

In a preferred embodiment, the nucleic acid preferably includes at least one universal base. Universal bases are those that can substitute for any of the five natural bases, that is, universal bases will basepair with all natural bases, preferably equally well. Suitable universal bases include, but are not limited to, inosine, hypoxanthine, 5-nitroindole, acylic 5-nitroindole, 4-nitropyrazole, 4-nitroimidazole and 3-nitropyrrole. See Loakes et al., Nucleic Acid Res. 22:4039 (1994); Van Aerschol et al., Nucleic Acid Res. 23:4363 (1995); Nichols et al., Nature 369:492 (1994); Berstrom et al., Nucleic Acid Res. 25:1935 (1997); Loakes et al., Nucleic Acid Res. 23:2361 (1995); Loakes et al., J. Mol. Biol. 270:426 (1997); and Fotin et al., Nucleic Acid Res. 26:1515 (1998); and references cited therein, all of which are expressly incorporated by reference.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made.

Particularly preferred are peptide nucleic acids (PNA) which includes peptide nucleic acid analogs. These backbones are substantially non-ionic under neutral conditions, in contrast to the highly charged phosphodiester backbone of naturally occurring nucleic acids. This results in two advantages. First, the PNA backbone exhibits improved hybridization kinetics. PNAs have larger changes in the melting temperature (Tm) for mismatched versus perfectly matched basepairs. DNA and RNA typically exhibit a 2–4° C. drop in Tm for an internal mismatch. With the non-ionic PNA backbone, the drop is closer to 7–9° C. This allows for better detection of mismatches. Similarly, due to their non-ionic nature, hybridization of the bases attached to these backbones is relatively insensitive to salt concentration.

The nucleic acids may be single stranded or double stranded, as specified, or contain portions of both double stranded or single stranded sequence. Thus, for example, when the target sequence is a polyadenylated mRNA, the hybridization complex comprising the target probe has a double stranded portion, where the target probe is hybridized, and one or more single stranded portions, including the poly(A) portion. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc. A preferred embodiment utilizes isocytosine and isoguanine in nucleic acids designed to be complementary to other probes, rather than target sequences, as this reduces non-specific hybridization, as is generally described in U.S. Pat. No.

5,681,702. As used herein, the term "nucleoside" includes nucleotides as well as nucleoside and nucleotide analogs, and modified nucleosides such as amino modified nucleosides. In addition, "nucleoside" includes non-naturally occuring analog structures. Thus for example the individual units of a peptide nucleic acid, each containing a base, are referred to herein as a nucleoside.

In a preferred embodiment, the compositions and methods of the invention are directed to the detection of target sequences. The term "target sequence" or "target nucleic acid" or grammatical equivalents herein means a nucleic acid sequence on a single strand of nucleic acid. The target sequence may be a portion of a gene, a regulatory sequence, genomic DNA (gDNA), cDNA, RNA including mRNA and rRNA, or others, with polyadenylated mRNA being particular preferred in some embodiments. As is outlined herein, the target sequence may be a target sequence from a sample, or a secondary target such as an amplicon, which is the product of an amplification reaction such as PCR or an RNA polymerase reaction. Thus, for example, a target sequence from a sample is amplified to produce an amplicon that is detected. The target sequence may be any length, with the understanding that longer sequences are more specific. As will be appreciated by those in the art, the complementary target sequence may take many forms. For example, it may be contained within a larger nucleic acid sequence, i.e. all or part of a gene or mRNA, a restriction fragment of a plasmid or genomic DNA, among others. Particularly preferred target sequences in the present invention include genomic DNA, polyadenylated mRNA, and alternatively spliced RNAs. As is outlined more fully below, probes are made to hybridize to target sequences to determine the presence, absence, quantity or sequence of a target sequence in a sample. Generally speaking, this term will be understood by those skilled in the art.

The target sequence may also be comprised of different target domains, that may be adjacent (i.e. contiguous) or separated. The terms "first" and "second" are not meant to confer an orientation of the sequences with respect to the 5'-3' orientation of the target sequence. For example, assuming a 5'–3' orientation of the complementary target sequence, the first target domain may be located either 5' to the second domain, or 3' to the second domain. In addition, as will be appreciated by those in the art, the probes on the surface of the array (e.g. attached to the microspheres) may be attached in either orientation, either such that they have a free 3' end or a free 5' end; in some embodiments, the probes can be attached at one ore more internal positions, or at both ends.

In a preferred embodiment the invention is directed to target sequences that comprise one or more positions for which sequence information is desired, generally referred to herein as the "detection position" or "detection locus". In a preferred embodiment, the detection position is a single nucleotide (sometimes referred to as a single nucleotide polymorphism (SNP)), although in some embodiments, it may comprise a plurality of nucleotides, either contiguous with each other or separated by one or more nucleotides. By "plurality" as used herein is meant at least two. As used herein, the base of a probe (e.g. the target probe) which basepairs with a detection position base in a hybrid is termed a "readout position" or an "interrogation position". Thus, the target sequence comprises a detection position and the target probe comprises a readout position.

In a preferred embodiment, the use of competitive hybridization target probes is done to elucidate either the identity of the nucleotide(s) at the detection position or the presence of a mismatch.

It should be noted in this context that "mismatch" is a relative term and meant to indicate a difference in the identity of a base at a particular position, termed the "detection position" herein, between two sequences. In general, sequences that differ from wild type sequences are referred to as mismatches. However, particularly in the case of SNPS, what constitutes "wild type" may be difficult to determine as multiple alleles can be relatively frequently observed in the population, and thus "mismatch" in this context requires the artificial adoption of one sequence as a standard. Thus, for the purposes of this invention, sequences are referred to herein as "match" and "mismatch". Thus, the present invention may be used to detect substitutions, insertions or deletions as compared to a wild-type sequence. That is, all other parameters being equal, a perfectly complementary readout target probe (a "match probe") will in general be more stable and have a slower off rate than a target probe comprising a mismatch (a "mismatch probe") at any particular temperature.

In some embodiments, as outlined below, the target analytes (or target probes, in some instances) may be attached to a solid support prior to contact with the target probes (or to remove unhybridized target probes, etc.). In this embodiment, the target analyte may comprise a purification tag. By "purification tag" herein is meant a moiety which can be used to purify a strand of nucleic acid, usually via attachment to a solid support as outlined herein. Suitable purification tags include members of binding partner pairs. For example, the tag may be a hapten or antigen, which will bind its binding partner. In a preferred embodiment, the binding partner can be attached to a solid support as depicted herein and in the figures. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid—nucleic acid binding proteins pairs are also useful. In general, the smaller of the pair is attached to the NTP for incorporation into the primer. Preferred binding partner pairs include, but are not limited to, biotin (or imino-biotin) and streptavidin, digeoxinin and Abs, and Prolinx™ reagents (see www.prolinxinc.com/ie4/home.hmtl).

In a preferred embodiment, the binding partner pair comprises biotin or imino-biotin and streptavidin. Iminobiotin is particularly preferred as imino-biotin disassociates from streptavidin in pH 4.0 buffer while biotin requires harsh denaturants (e.g. 6 M guanidinium HCl, pH 1.5 or 90% formamide at 95° C.).

The present invention provides methods and compositions directed to the multiplex amplification and detection of target sequences utilizing target probes.

Accordingly, the invention provides a number of different primers and probes. Many of the probes and primers of the present invention are designed to have at least a portion that binds substantially specifically to a target analyte (sometimes referred to herein as a bioactive agent (particularly in the case wherein the target analyte is not a nucleic acid) or a target specific portion). That is the probes are constructed so as to contain a target specific portion: a portion that binds to the target analyte specifically, i.e. with high affinity. This target specific portion can be any type of molecule so long as it specifically binds the target and can be attached to the rest of a target probe, namely a nucleic acid sequence that preferably includes an adapter sequence and at least one priming sequence.

In a preferred embodiment, when the target analyte is a protein, for example, the target specific portion ("bioactive agent") may include other protein molecules such as antibodies, specific binding proteins or ligands such as growth factors. Also, the target-specific portion can be an aptamer as is known in the art, i.e. a nucleotide sequence that binds with high affinity to a protein.

In a preferred embodiment, the binding of the bioactive agent and the target analyte is specific; that is, the bioactive agent specifically binds to the target analyte. By "specifically bind" herein is meant that the agent binds the analyte, with specificity sufficient to differentiate between the analyte and other components or contaminants of the test sample. However, as will be appreciated by those in the art, it will be possible to detect analytes using binding which is not highly specific; for example, the systems may use different binding ligands, for example an array of different ligands, and detection of any particular analyte is via its "signature" of binding to a panel of binding ligands, similar to the manner in which "electronic noses" work. This finds particular utility in the detection of chemical analytes. The binding should be sufficient to remain bound under the conditions of the assay, including wash steps to remove non-specific binding, although in some embodiments, wash steps are not desired; i.e. for detecting low affinity binding partners. In some embodiments, for example in the detection of certain biomolecules, the dissociation constants of the analyte to the binding ligand will be less than about 10-4–10-6 M-1, with less than about 10-5 to 10-9 M-1 being preferred and less than about 10-7–10-9 M-1 being particularly preferred.

When nucleic acids are the target, the probes are designed to be complementary to all or a portion (domain) of a target sequence (either the target sequence of the sample or to other probe sequences, such as portions of amplicons, as is described below), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the bioactive agent portion of the probes are sufficiently complementary to all or part of the target sequences to hybridize under normal reaction conditions, and preferably give the required specificity. In a preferred embodiment the probes have a portion that is exactly complementary to the target nucleic acids.

A variety of hybridization conditions may be used in the present invention, including high, moderate and low stringency conditions; see for example Maniatis et al., Molecular Cloning: A Laboratory Manual, 2d Edition, 1989, and Short Protocols in Molecular Biology, ed. Ausubel, et al, hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point (Tm) for the specific sequence at a defined ionic strength and pH. The Tm is the temperature (under defined ionic strength, pH and nucleic acid concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of helix destabilizing agents such as formamide. The hybridization conditions may also vary when a non-ionic backbone, i.e. PNA is used, as is known in the art. In addition, cross-linking agents may be added after target binding to cross-link, i.e. covalently attach, the two strands of the hybridization complex.

In a preferred embodiment, the target probes further comprise one or more "adapter sequences" (sometimes referred to in the art as "zip codes") to allow the use of "universal arrays". That is, arrays are generated that contain capture probes that are not target specific, but rather specific to individual artificial adapter sequences. The adapter sequences are added to the target probes, nested between the priming sequences (when two priming sequences are used) or "downstream" of a single universal priming sequence, and thus are included in the amplicons. What is important is that the orientation of the priming sequence and the adapter sequence allows the amplification of the adapter sequence.

An "adapter sequence" is a sequence, generally exogeneous to the target sequences, e.g. artificial, that is designed to be substantially complementary (and preferably perfectly complementary) to a capture probe of a detection array. Generally the capture probe is immobilized to a solid support that can include microspheres or planar substrates such as plastic or glass slides as described herein for array supports. In one embodiment the use of adapter sequences allow the creation of more "universal" surfaces; that is, one standard array, comprising a finite set of capture probes can be made and used in any application. The end-user can customize the array by designing different soluble target probes, which, as will be appreciated by those in the art, is generally simpler and less costly. In a preferred embodiment, an array of different and usually artificial capture probes are made; that is, the capture probes do not have complementarity to known target sequences. The adapter sequences can then be incorporated in the target probes.

As will be appreciated by those in the art, the length of the adapter sequences will vary, depending on the desired "strength" of binding and the number of different adapters desired. In a preferred embodiment, adapter sequences range from about 6 to about 500 basepairs in length, with from about 8 to about 100 being preferred, and from about 10 to about 25 being particularly preferred.

In a preferred embodiment, the adapter sequence uniquely identifies the target analyte to which the target probe binds. That is, while the adapter sequence need not bind itself to the target analyte, the system allows for identification of the target analyte by detecting the presence of the adapter. Accordingly, following a binding or hybridization assay and washing, the probes including the adapters are amplified. Detection of the adapter then serves as an indication of the presence of the target analyte.

In one embodiment the adapter includes both an identifier region and a region that is complementary to capture probes on a universal array as described above. In this embodiment, the amplicon hybridizes to capture probes on a universal array. Detection of the adapter is accomplished following hybridization with a probe that is complementary to the adapter sequence. Preferably the probe is labeled as described herein.

In general, unique adapter sequences are used for each unique target analyte. That is, the elucidation or detection of a particular adapter sequence allows the identification of the target analyte to which the target probe containing that adapter sequence bound. However, in some cases, it is possible to "reuse" adapter sequences and have more than one target analyte share an adapter sequence.

In a preferred embodiment the adapters contain different sequences or properties that are indicative of a particular target molecule. That is, each adapter uniquely identifies a target analyte. As described above, the adapters are amplified to form amplicons. The adapter is detected as an indication of the presence of the target analyte.

The use of adapters in combination with amplification following a specific binding event allows for highly multiplexed reactions to be performed.

Also, the probes are constructed so as to contain the necessary priming site or sites for the subsequent amplification scheme. In a preferred embodiment the priming sites are universal priming sites. By "universal priming site" or "universal priming sequences" herein is meant a sequence of the probe that will bind a primer for amplification.

In a preferred embodiment, one universal priming sequence or site is used. In this embodiment, a preferred universal priming sequence is the RNA polymerase T7 sequence, that allows the T7 RNA polymerase make RNA copies of the adapter sequence as outlined below.

In a preferred embodiment, for example when amplification methods requiring two primers such as PCR are used, each probe preferably comprises an upstream universal priming site (UUP) and a downstream universal priming site (DUP). Again, "upstream" and "downstream" are not meant to convey a particular 5'–3' orientation, and will depend on the orientation of the system. Preferably, only a single UUP sequence and a single DUP sequence is used in a probe set, although as will be appreciated by those in the art, different assays or different multiplexing analysis may utilize a plurality of universal priming sequences. In addition, the universal priming sites are preferably located at the 5' and 3' termini of the target probe (or the ligated probe), as only sequences flanked by priming sequences will be amplified.

In addition, universal priming sequences are generally chosen to be as unique as possible given the particular assays and host genomes to ensure specificity of the assay. However, as will be appreciated by those in the art, sets of priming sequences/primers may be used; that is, one reaction may utilize 500 target probes with a first priming sequence or set of sequences, and an additional 500 probes with a second sequence or set of sequences.

As will be appreciated by those in the art, when two priming sequences are used, the orientation of the two priming sites is different. That is, one PCR primer will directly hybridize to the first priming site, while the other PCR primer will hybridize to the complement of the second priming site. Stated differently, the first priming site is in sense orientation, and the second priming site is in antisense orientation.

The size of the primer and probe nucleic acid may vary, as will be appreciated by those in the art with each portion of the probe and the total length of the probe in general varying from 5 to 500 nucleotides in length. Each portion is preferably between 10 and 100 being preferred, between 15 and 50 being particularly preferred, and from 10 to 35 being especially preferred, depending on the use and amplification technique. Thus, for example, the universal priming site(s) of the probes are each preferably about 15–20 nucleotides in length, with 18 being especially preferred. The adapter sequences of the probes are preferably from 15–25 nucleotides in length, with 20 being especially preferred. The target specific portion of the probe is preferably from 15–50 nucleotides in length. In addition, the primer may include an additional amplification priming site. In a preferred embodiment the additional amplification priming site is a T7 RNA polymerase priming site.

Accordingly, the present invention provides first target probe sets. By "probe set" herein is meant a plurality of target probes that are used in a particular multiplexed assay. In this context, plurality means at least two, with more than 10 being preferred, depending on the assay, sample and purpose of the test. In one embodiment the probe set includes more than 100, with more than 500 probes being preferred and more than 1000 being particularly preferred. In a particularly preferred embodiment each probe contains at least 5000, with more than 10,000 probes being most preferred.

Accordingly, the present invention provides first target probe sets that comprise at least a first universal priming site.

In a preferred embodiment, the target probe may also comprise a label sequence, i.e. a sequence that can be used to bind label probes and is substantially complementary to a label probe. This is sometimes referred to in the art as "sandwich-type" assays. That is, by incorporating a label sequence into the target probe, which is then amplified and present in the amplicons, a label probe comprising primary (or secondary) labels can be added to the mixture, either before addition to the array or after. This allows the use of high concentrations of label probes for efficient hybridization. In one embodiment, it is possible to use the same label sequence and label probe for all target probes on an array; alternatively, different target probes can have a different label sequence. Similarly, the use of different label sequences can facilitate quality control; for example, one label sequence (and one color) can be used for one strand of the target, and a different label sequence (with a different color) for the other; only if both colors are present at the same basic level is a positive called.

Thus, the present invention provides target probes that comprise universal priming sequences, bioactive agents (e.g. target specific portion(s)), adapter sequence(s), optionally an additional amplification priming sequence such as T7 RNA priming sequence and optionally label sequences. These target probes are then added to the target sequences to form hybridization complexes. As will be appreciated by those in the art, when nucleic acids are the target, the hybridization complexes contain portions that are double stranded (the target-specific sequences of the target probes hybridized to a portion of the target sequence) and portions that are single stranded (the ends of the target probes comprising the universal priming sequences and the adapter sequences, and any unhybridized portion of the target sequence, such as poly(A) tails, as outlined herein).

As will be appreciated by those in the art, the systems of the invention can take on a wide variety of configurations, including systems that rely on the initial immobilization of the target analyte (solid phase assays) and solution based assays.

Solid Phase Assays

In a preferred embodiment, the target analyte is immobilized on the surface. That is, the target analytes including proteins or target nucleic acids or target sequences are immobilized on a substrate or capture surface. Attachment may be performed in a variety of ways, as will be appreciated by those in the art, including, but not limited to, chemical or affinity capture (for example, including the incorporation attachment moieties such as derivatized nucleotides such as AminoLink™ or biotinylated nucleotides that can then be used to attach the nucleic acid to a surface, as well as affinity capture by hybridization), cross-linking, and electrostatic attachment, etc. When the target analyte is polyadenylated mRNA, supports comprising poly(T) sequences can be used. That is, an attachment moiety is attached to the target analyte that allows for attachment to the substrate. By "attachment moiety" is meant a molecule or substance that mediates attachment of the target analyte to the substrate. In a preferred embodiment, affinity capture is used to attach the nucleic acids to the support. For example, nucleic acids or proteinscan be derivatized, for example with one member of a binding pair, and the support derivatized with the other member, i.e. a complementary member, of a binding pair. For example, the nucleic acids may be biotinylated (for example using enzymatic incorporation of biotinylated nucleotides, or by photoactivated cross-linking of biotin). In a preferred embodiment the target nucleic acids are photobiotinylated. In one preferred embodiment the target nucleic acids are photobiotinylated with PHOTOPROBE™ Biotin Reagents (Vector Laboratories). Biotinylated nucleic acids can then be captured on streptavidin-coated surfaces, as is known in the art. In one embodiment the surfaces or supports are beads to which the nucleic acids are attached. In a particularly preferred embodiment the beads are magnetic beads. Similarly, other hapten-receptor combinations can be used, such as digoxigenin and anti-digoxigenin antibodies. Alternatively, chemical groups can be added in the form of derivatized nucleotides, that can then be used to add the nucleic acid to the surface.

Similarly, affinity capture utilizing hybridization can be used to attach nucleic acids to surface or bead. For example, a polyA tract can be attached by polymerization with terminal transferase, or via ligation of an oligoA linker, as is known in the art. This then allows for hybridization with an immobilized poly-T tract. Alternatively, chemical crosslinking may be done, for example by photoactivated crosslinking of thymidine to reactive groups, as is known in the art.

Preferred attachments are covalent, although even relatively weak interactions (i.e. non-covalent) can be sufficient to attach a nucleic acid to a surface, if there are multiple sites of attachment per each nucleic acid. Thus, for example, electrostatic interactions can be used for attachment, for example by having beads carrying the opposite charge to the bioactive agent.

A preferred embodiment utilizes covalent attachment of the target sequences to a support. As is known in the art, there are a wide variety of methods used to covalently attach nucleic acids to surfaces. A preferred embodiment utilizes the incorporation of a chemical functional group into the nucleic acid, followed by reaction with a derivatized or activated surface. Examples include, but are not limited to AminoLink™.

By "capture surface", "target substrate" or "target support" or other grammatical equivalents herein is meant any material to which a target analyte can be attached. The targets can be attached either directly or indirectly as described herein. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, and a variety of other polymers. Preferably the substrates include microfuge tubes, i.e. Eppendorf tubes. In one embodiment the substrates include beads or microspheres. In one embodiment the beads or microspheres are magnetic. In one embodiment the substrates are derivatized to accommodate attachment of the target nucleic acids to the substrate.

The configuration of the target support is not crucial. What is important is that the target analytes are immobilized to the target support and can be manipulated. That is, the support should be amenable to a variety of reactions as described herein. While the target substrate can be flat (planar), other configurations of substrates may be used as well; for example, target analytes can be attached to beads or microspheres that can be deposited in reaction tubes or vessels or wells. That is, the target substrate may be microspheres to which the target analytes are attached. The microspheres can then be distributed on a surface. In some embodiments the surface contains reaction wells into which the beads are distributed, for example microtiter plates as are known in the art and as described herein.

Once the target analytes, i.e. genomic DNA or proteins, are applied to or immobilized on the surface, the target analytes are contacted with probes for analyses, including detection or genotyping. That is, the appropriate probes necessary for detection of the target analyte or for the mutation detection reactions are next introduced to the immobilized sample.

For the assays described herein, the assays may be run under a variety of experimental conditions, as will be appreciated by those in the art. A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding. Various blocking and washing steps may be utilized as is known in the art.

Following binding or hybridization of the bioactive agent portion of the target probe to the target analyte, unhybridized probes are removed by a washing step. In a preferred embodiment the wash step is a stringent wash step. That is, in the preferred embodiment of an enzymatic based mutation detection reaction, once the probes have been introduced under conditions to favor hybridization with the appropriate nucleic acid sequences, a stringent wash step is conducted. This wash removes unhybridized probes and reduces the overall complexity of the mixture. It is this step that ensures the success of the overall multiplexed reaction.

As will be appreciated by those in the art, when the target analyte is a nucleic acid, there are a wide variety of SNP detection reactions that can be done at this stage. In a preferred embodiment, different target probes are made with different interrogation bases in the target-specific domain of the probe. The wash step is done under conditions to wash away imperfect matches between the interrogation base of the target probe and the detection position of the target sequence.

In a preferred embodiment when nucleic acids are the target, a plurality of target probes (sometimes referred to herein as "readout target probes") are used to identify the base at the detection position. In this embodiment, each different readout probe comprises a different base at the position that will hybridize to the detection position of the target sequence (herein referred to as the readout or interrogation position) and a different adapter sequence for each different readout position. In this way, differential hybridization of the readout target probes, depending on the sequence of the target, results in identification of the base at the detection position. In this embodiment, the readout probes are contacted with the array again under conditions that allow discrimination between match and mismatch, and the unhybridized probes are removed, etc.

Accordingly, by using different readout target probes, each with a different base at the readout position and each with a different adapter, the identification of the base at the detection position is elucidated. Thus, in a preferred embodiment, a set of readout probes are used, each comprising a different base at the readout position.

In a preferred embodiment, each readout target probe has a different adapter sequence. That is, readout target probes comprising adenine at the readout position will have a first adapter, probes with guanine at the readout position will have a second adapter, etc., such that each target probe that hybridizes to the target sequence will bind to a different address on the array. This can allow the use of the same label for each reaction.

The number of readout target probes used will vary depending on the end use of the assay. For example, many SNPs are biallelic, and thus two readout target probes, each comprising an interrogation base that will basepair with one of the detection position bases. For sequencing, for example, for the discovery of SNPs, a set of four readout probes are used.

In this embodiment, sensitivity to variations in stringency parameters are used to determine either the identity of the nucleotide(s) at the detection position or the presence of a mismatch. As a preliminary matter, the use of different stringency conditions such as variations in temperature and buffer composition to determine the presence or absence of mismatches in double stranded hybrids comprising a single stranded target sequence and a probe is well known.

With particular regard to temperature, as is known in the art, differences in the number of hydrogen bonds as a function of basepairing between perfect matches and mismatches can be exploited as a result of their different Tms (the temperature at which 50% of the hybrid is denatured). Accordingly, a hybrid comprising perfect complementarity will melt at a higher temperature than one comprising at least one mismatch, all other parameters being equal. (It should be noted that for the purposes of the discussion herein, all other parameters (i.e. length of the hybrid, nature of the backbone (i.e. naturally occuring or nucleic acid analog), the assay solution composition and the composition of the bases, including G-C content are kept constant). However, as will be appreciated by those in the art, these factors may be varied as well, and then taken into account.)

In general, as outlined herein, high stringency conditions are those that result in perfect matches remaining in hybridization complexes, while imperfect matches melt off. Similarly, low stringency conditions are those that allow the formation of hybridization complexes with both perfect and imperfect matches. High stringency conditions are known in the art as outlined above.

As will be appreciated by those in the art, mismatch detection using temperature may proceed in a variety of ways.

Similarly, variations in buffer composition may be used to elucidate the presence or absence of a mismatch at the detection position. Suitable conditions include, but are not limited to, formamide concentration. Thus, for example, "low" or "permissive" stringency conditions include formamide concentrations of 0 to 10%, while "high" or "stringent" conditions utilize formamide concentrations of $\geq 40\%$. Low stringency conditions include NaCl concentrations of $\geq 1$ M, and high stringency conditions include concentrations of $\leq 0.3$ M. Furthermore, low stringency conditions include $MgCl_2$ concentrations of $\geq 10$ mM, moderate stringency as 1–10 mM, and high stringency conditions include concentrations of $\leq 1$ mM.

In this embodiment, as for temperature, a plurality of readout probes may be used, with different bases in the readout position and different adapters. Running the assays under the permissive conditions and repeating under stringent conditions will allow the elucidation of the base at the detection position.

Thus, the washing is performed under stringency conditions which allows formation of the first hybridization complex only between probes and complementary target sequences. As outlined above, stringency can be controlled by altering a step parameter that is a thermodynamic variable, including, but not limited to, temperature, formamide concentration, salt concentration, chaotropic salt concentration, pH, organic solvent concentration, etc.

These parameters may also be used to control non-specific binding, as is generally outlined in U.S. Pat. No. 5,681,697. Thus it may be desirable to perform certain steps at higher stringency conditions to reduce non-specific binding.

In a preferred embodiment, the target sequence may be immobilized after the formation of the hybridization complexes, ligation complexes and/or ligated complexes. That is, the probes can be added to the targets in solution, enzymes added as needed, etc. After the hybridization complexes are formed and/or ligated, the hybridization complexes can be added to supports comprising the binding partners and the unhybridized probes removed.

In this embodiment, particularly preferred binding ligand/binding partner pairs are biotin and streptavidin or avidin, antigens and antibodies.

As described above, once the hybridization complexes are formed, unhybridized probes are removed. This is important to increase the level of multiplexing in the assay. In addition, as all target probes may form some unpredictable structures that will complicate the amplification using the universal priming sequences. Thus to ensure specificity (e.g. that target probes directed to target sequences that are not present in the sample are not amplified and detected), it is important to remove all the nonhybridized probes. As will be appreciated by those in the art, this may be done in a variety of ways, including methods based on the target sequence, methods utilizing double stranded specific moieties, and methods based on probe design and content. Preferably the method includes a stringent wash step.

Once the non-hybridized probes (and additionally, if preferred, other sequences from the sample that are not of interest) are removed, the hybridization complexes are denatured and the target probes are amplified to form amplicons, which are then detected. This can be done in one of several ways as outlined below. In addition, as outlined below, labels can be incorporated into the amplicons in a variety of ways.

Accordingly, this embodiment can be run in several modes. In a preferred embodiment, only a single probe is used, comprising (as outlined herein), at least a first UUP, an adapter sequence, and a target-specific portion, i.e. a target specific moeity or bioactive agent. When nucleotides are the target molecule the target-specific portion includes nucleic acids comprising a first base at the readout position, and in some embodiments a DUP. This probe is contacted with the target analyte under conditions (whether thermal or otherwise) such that specific binding occurs. In a preferred embodiment, when nucleic acids are the target, a hybridization complex is formed only when a perfect match between the detection position of the target and the readout position of the probe is present. The non-hybridized or non-bound probes are then removed as outlined herein. That is, after the wash step, only the properly hybridized probes should remain. In one embodiment when nucleic acids are the target, the hybridized probes must then be separated from the captured sample nucleic acid. This is done via a stringent wash step or denaturation step. The sample nucleic acid is left behind on the capture surface, and can be used again. In an alternative embodiment, although not preferred, the hybridized probe is not removed. it is not necessary to remove the probes when the priming sites and adapter sequences do not hybridize with the target. The probe is then amplified as outlined herein, and detected. In a preferred embodiment the amplified product(s), i.e. amplicons, are detected as an indication of the presence of the target analyte.

When molecules besides nucleic acids are the target, the bound probes need not be removed from the binding complex prior to amplification. That is, amplification can proceed while the probes are bound to the target. Without being bound be theory, it is thought that amplification can proceed because the nucleotides are not hybridized with a complementary strand. As such, they are free to hybridize with amplification primers.

As noted above, the target sequence may be immobilized either before or after the formation of the hybridization complex, but preferably it is immobilized on a surface or support comprising the binding partner of the binding ligand prior to the formation of the hybridization complex with the probe(s) of the invention. For example, a preferred embodiment utilizes binding partner coated reaction vessels such as eppendorf tubes or microtiter wells. Alternatively, the support may be in the form of beads, including magnetic beads. In this embodiment, the target sequences are immobilized, the target probes are added to form hybridization complexes. Unhybridized probes are then removed through washing steps, and the bound probes (e.g. either target probes, ligated probes, or ligated RCA probes) are then eluted off the support, usually through the use of elevated temperature or buffer conditions (pH, salt, etc.).

Once the non-hybridized probes (and additionally, if preferred, other sequences from the sample that are not of interest) are removed, the hybridization complexes are denatured and the target probes are amplified to form amplicons, which are then detected. This can be done in one of several ways, including PCR amplification and rolling circle amplification. Also, the probes can be amplified by known methods (exponential or linear amplification techniques such as PCR, Invader, ESPIA (also known as SPIA), T7), using the one or more priming sites provided on the probes. As noted herein, the probes are constructed so as to contain the necessary primer sites to permit this amplification. In a preferred embodiment, universal primers are used. Amplification provides the signal strength and dynamic range necessary for detection of the mutation-detection probes. In addition, as outlined below, labels can be incorporated into the amplicons in a variety of ways.

In a preferred embodiment, no ligation assay for genotyping is done, that is, no ligase is added. However, as will be appreciated by those in the art, ligation reactions for other purposes may be don.

In a preferred embodiment, a linear amplification scheme known as ESPIA, or SPIA is applied. This amplification technique is disclosed in WO 01/20035 A2 and U.S. application Ser. No. 6,251,639, which are incorporated by reference herein. Generally, the method includes hybridizing chimeric RNA/DNA amplification primers to the probes. Preferably the DNA portion of the probe is 3' to the RNA. Optionally the method includes hybridizing a polynucleotide comprising a termination polynucleotide sequence to a region of the template that is 5' with respect to hybridization of the composite primer to the template. Following hybridization of the primer to the template, the primer is extended with DNA polymerase. Subsequently, the RNA is cleaved from the composite primer with an enzyme that cleaves RNA from an RNA/DNA hybrid. Subsequently, an additional RNA/DNA chimeric primer is hybridized to the template such that the first extended primer is displaced from the target probe. The extension reaction is repeated, whereby multiple copies of the probe sequence are generated.

In a preferred embodiment, the target amplification technique is PCR. The polymerase chain reaction (PCR) is widely used and described, and involves the use of primer extension combined with thermal cycling to amplify a target sequence; see U.S. Pat. Nos. 4,683,195 and 4,683,202, and PCR Essential Data, J. W. Wiley & sons, Ed. C. R. Newton, 1995, all of which are incorporated by reference.

In general, PCR may be briefly described as follows. The double stranded hybridization complex is denatured, generally by raising the temperature, and then cooled in the presence of an excess of a PCR primer, which then hybridizes to the first universal priming site. A DNA polymerase then acts to extend the primer with dNTPs, resulting in the synthesis of a new strand forming a hybridization complex. The sample is then heated again, to disassociate the hybridization complex, and the process is repeated. By using a second PCR primer for the complementary target strand that hybridizes to the second universal priming site, rapid and exponential amplification occurs. Thus PCR steps are denaturation, annealing and extension. The particulars of PCR are well known, and include the use of a thermostable polymerase such as Taq I polymerase and thermal cycling. Suitable DNA polymerases include, but are not limited to, the Klenow fragment of DNA polymerase I, SEQUENASE 1.0 and SEQUENASE 2.0 (U.S. Biochemical), T5 DNA polymerase and Ph129 DNA polymerase.

The reaction is initiated by introducing the target probe comprising the target sequence to a solution comprising the universal primers, a polymerase and a set of nucleotides. By "nucleotide" in this context herein is meant a deoxynucleoside-triphosphate (also called deoxynucleotides or dNTPs, e.g. dATP, dTTP, dCTP and dGTP). In some embodiments, as outlined below, one or more of the nucleotides may comprise a detectable label, which may be either a primary or a secondary label. In addition, the nucleotides may be nucleotide analogs, depending on the configuration of the system. Similarly, the primers may comprise a primary or secondary label.

Accordingly, the PCR reaction requires at least one PCR primer, a polymerase, and a set of dNTPs. As outlined herein, the primers may comprise the label, or one or more of the dNTPs may comprise a label.

In a preferred embodiment, the methods of the invention include a rolling circle amplification (RCA) step. This may be done in several ways. In one embodiment, either single target probes or ligated probes can be used in the genotyping part of the assay, followed by RCA instead of PCR. Alternatively, and more preferably, the RCA reaction forms part of the genotyping reaction and can be used for both genotyping and amplification in the methods of the reaction.

In a preferred embodiment, the methods rely on rolling circle amplification. "Rolling circle amplification" is based on extension of a circular probe that has hybridized to a target sequence. A polymerase is added that extends the probe sequence. As the circular probe has no terminus, the polymerase repeatedly extends the circular probe resulting in concatamers of the circular probe. As such, the probe is amplified. Rolling-circle amplification is generally described in Baner et al. (1998) *Nuc. Acids Res.* 26:5073–5078; Barany, F. (1991) *Proc. Natl. Acad. Sci. USA* 88:189–193; and Lizardi et al. (1998) *Nat. Genet.* 19:225–232, all of which are incorporated by reference in their entirety.

In general, RCA may be described in two ways, as generally depicted in FIGS. 9 and 10. First, as is outlined in more detail below, a single target probe is hybridized with a target nucleic acid. Each terminus of the probe hybridizes adjacently on the target nucleic acid and the OLA assay as described above occurs. When ligated, the probe is circularized while hybridized to the target nucleic acid.

Addition of a polymerase results in extension of the circular probe. However, since the probe has no terminus, the polymerase continues to extend the probe repeatedly. Thus results in amplification of the circular probe.

A second alternative approach involves a two step process. In this embodiment, two ligation probes are initially ligated together, each containing a universal priming sequence. A rolling circle primer is then added, which has portions that will hybridize to the universal priming sequences. The presence of the ligase then causes the original probe to circularize, using the rolling circle primer as the polymerase primer, which is then amplified as above.

These embodiments also have the advantage that unligated probes need not necessarily be removed, as in the absence of the target, no significant amplification will occur. These benefits may be maximized by the design of the probes; for example, in the first embodiment, when there is a single target probe, placing the universal priming site close to the 5' end of the probe since this will only serve to generate short, truncated pieces, without adapters, in the absence of the ligation reaction.

Accordingly, in an preferred embodiment, a single oligonucleotide is used both for OLA and as the circular template for RCA (referred to herein as a "padlock probe" or a "RCA probe"). That is, each terminus of the oligonucleotide contains sequence complementary to the target nucleic acid and functions as an OLA primer as described above. That is, the first end of the RCA probe is substantially complementary to a first target domain, and the second end of the RCA probe is substantially complementary to a second target domain, adjacent to the first domain. Hybridization of the oligonucleotide to the target nucleic acid results in the formation of a hybridization complex. Ligation of the "primers" (which are the discrete ends of a single oligonucleotide) results in the formation of a modified hybridization complex containing a circular probe i.e. an RCA template complex. That is, the oligonucleotide is circularized while still hybridized with the target nucleic acid. This serves as a circular template for RCA. Addition of a primer and a polymerase to the RCA template complex results in the formation of an amplicon.

Labeling of the amplicon can be accomplished in a variety of ways; for example, the polymerase may incorporate labeled nucleotides, or alternatively, a label probe is used that is substantially complementary to a portion of the RCA probe and comprises at least one label is used, as is generally outlined herein.

The polymerase can be any polymerase, but is preferably one lacking 3' exonuclease activity (3' exo⁻). Examples of suitable polymerase include but are not limited to exonuclease minus DNA Polymerase I large (Klenow) Fragment, Ph129 DNA polymerase, Taq DNA Polymerase and the like. In addition, in some embodiments, a polymerase that will replicate single-stranded DNA (i.e. without a primer forming a double stranded section) can be used. In addition, while some embodiments utilize ligase, such as in the OLA or RCA, in some embodiments amplification alone is preferred. That is amplification is performed without a ligase step and without including a ligase enzyme.

In a preferred embodiment, the RCA probe contains an adapter sequence as outlined herein, with adapter capture probes on the array, for example on a microsphere when microsphere arrays are being used. Alternatively, unique portions of the RCA probes, for example all or part of the sequence corresponding to the target sequence, can be used to bind to a capture probe.

In a preferred embodiment, the padlock probe contains a restriction site. The restriction endonuclease site allows for cleavage of the long concatamers that are typically the result of RCA into smaller individual units that hybridize either more efficiently or faster to surface bound capture probes. Thus, following RCA, the product nucleic acid is contacted with the appropriate restriction endonuclease. This results in cleavage of the product nucleic acid into smaller fragments. The fragments are then hybridized with the capture probe that is immobilized resulting in a concentration of product fragments onto the microsphere. Again, as outlined herein, these fragments can be detected in one of two ways: either labelled nucleotides are incorporated during the replication step, or an additional label probe is added.

Thus, in a preferred embodiment, the padlock probe comprises a label sequence; i.e. a sequence that can be used to bind label probes and is substantially complementary to a label probe. In one embodiment, it is possible to use the same label sequence and label probe for all padlock probes on an array; alternatively, each padlock probe can have a different label sequence.

The padlock probe also contains a priming site for priming the RCA reaction. That is, each padlock probe comprises a sequence to which a primer nucleic acid hybridizes forming a template for the polymerase. The primer can be found in any portion of the circular probe. In a preferred embodiment, the primer is located at a discrete site in the probe. In this embodiment, the primer site in each distinct padlock probe is identical, e.g. is a universal priming site, although this is not required. Advantages of using primer sites with identical sequences include the ability to use only a single primer oligonucleotide to prime the RCA assay with a plurality of different hybridization complexes. That is, the padlock probe hybridizes uniquely to the target nucleic acid to which it is designed. A single primer hybridizes to all of the unique hybridization complexes forming a priming site for the polymerase. RCA then proceeds from an identical locus within each unique padlock probe of the hybridization complexes.

In an alternative embodiment, the primer site can overlap, encompass, or reside within any of the above-described elements of the padlock probe. That is, the primer can be found, for example, overlapping or within the restriction site or the identifier sequence. In this embodiment, it is necessary that the primer nucleic acid is designed to base pair with the chosen primer site.

Thus, the padlock probe of the invention contains at each terminus, sequences corresponding to OLA primers. The intervening sequence of the padlock probe contain in no particular order, an adapter sequence and a restriction endonuclease site. In addition, the padlock probe contains a RCA priming site.

Thus, in a preferred embodiment the OLA/RCA is performed in solution followed by restriction endonuclease cleavage of the RCA product. The cleaved product is then applied to an array comprising beads, each bead comprising a probe complementary to the adapter sequence located in the padlock probe. The amplified adapter sequence correlates with a particular target nucleic acid. Thus the incorporation of an endonuclease site allows the generation of short, easily hybridizable sequences. Furthermore, the unique adapter sequence in each rolling circle padlock probe sequence allows diverse sets of nucleic acid sequences to be analyzed in parallel on an array, since each sequence is resolved on the basis of hybridization specificity.

Thus, the present invention provides for the generation of amplicons (sometimes referred to herein as secondary targets).

In a preferred embodiment, the amplicons are labeled with a detection label. By "detection label" or "detectable label" herein is meant a moiety that allows detection. This may be a primary label or a secondary label. Accordingly, detection labels may be primary labels (i.e. directly detectable) or secondary labels (indirectly detectable).

In a preferred embodiment, the detection label is a primary label. A primary label is one that can be directly detected, such as a fluorophore. In general, labels fall into three classes: a) isotopic labels, which may be radioactive or heavy isotopes; b) magnetic, electrical, thermal labels; and c) colored or luminescent dyes. Labels can also include enzymes (horseradish peroxidase, etc.) and magnetic particles. Preferred labels include chromophores or phosphors but are preferably fluorescent dyes. Suitable dyes for use in the invention include, but are not limited to, fluorescent lanthanide complexes, including those of Europium and Terbium, fluorescein, rhodamine, tetramethylrhodamine, eosin, erythrosin, coumarin, methyl-coumarins, quantum dots (also referred to as "nanocrystals": see U.S. Ser. No. 09/315,584, hereby incorporated by reference), pyrene, Malacite green, stilbene, Lucifer Yellow, Cascade Blue™, Texas Red, Cy dyes (Cy3, Cy5, etc.), alexa dyes, phycoerythin, bodipy, and others described in the 6th Edition of the Molecular Probes Handbook by Richard P. Haugland, hereby expressly incorporated by reference.

In a preferred embodiment, a secondary detectable label is used. A secondary label is one that is indirectly detected; for example, a secondary label can bind or react with a primary label for detection, can act on an additional product to generate a primary label (e.g. enzymes), or may allow the separation of the compound comprising the secondary label from unlabeled materials, etc. Secondary labels include, but are not limited to, one of a binding partner pair such as biotin/streptavidin; chemically modifiable moieties; nuclease inhibitors, enzymes such as horseradish peroxidase, alkaline phosphatases, luciferases, etc.

In a preferred embodiment, the secondary label is a binding partner pair. For example, the label may be a hapten or antigen, which will bind its binding partner. In a preferred embodiment, the binding partner can be attached to a solid support to allow separation of extended and non-extended primers. For example, suitable binding partner pairs include, but are not limited to: antigens (such as proteins (including peptides)) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid—nucleic acid binding proteins pairs are also useful. In general, the smaller of the pair is attached to the NTP for incorporation into the primer. Preferred binding partner pairs include, but are not limited to, biotin (or imino-biotin) and streptavidin, digeoxinin and Abs, and Prolinx™ reagents (see www.prolinxinc.com/ie4/home.hmtl).

In a preferred embodiment, the binding partner pair comprises biotin or imino-biotin and streptavidin. Imino-biotin is particularly preferred as imino-biotin disassociates from streptavidin in pH 4.0 buffer while biotin requires harsh denaturants (e.g. 6 M guanidinium HCl, pH 1.5 or 90% formamide at 95° C.).

In a preferred embodiment, the binding partner pair comprises a primary detection label (for example, attached to the NTP and therefore to the amplicon) and an antibody that will specifically bind to the primary detection label. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$–$10^{-6}$ $M^{-1}$, with less than about $10^{-5}$ to $10^{-9}$ $M^{-1}$ being preferred and less than about $10^{-7}$–$10^{-9}$ $M^{-1}$ being particularly preferred.

In a preferred embodiment, the secondary label is a chemically modifiable moiety. In this embodiment, labels comprising reactive functional groups are incorporated into the nucleic acid. The functional group can then be subsequently labeled with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers as are known in the art; for example, homo-or hetero-bifunctional linkers as are well known (see 1994 Pierce Chemical Company catalog, technical section on cross-linkers, pages 155–200, incorporated herein by reference).

As outlined herein, labeling can occur in a variety of ways, as will be appreciated by those in the art. In general, labeling can occur in one of three ways: labels are incorporated into primers such that the amplification reaction results in amplicons that comprise the labels; labels are attached to dNTPs and incorporated by the polymerase into the amplicons; or the amplicons comprise a label sequence that is used to hybridize a label probe, and the label probe comprises the labels. It should be noted that in the latter case, the label probe can be added either before the amplicons are contacted with an array or afterwards.

A preferred embodiment utilizes one primer comprising a biotin, that is used to bind a fluorescently labeled streptavidin.

In a preferred embodiment following amplification, the amplicons are subjected to an additional amplification step.

Preferably the additional amplification step is a T7 RNA polymerase reaction, although T7 amplification also can be the primary amplification step. The advantage of following the amplification step with an additional amplification step such as the T7 RNA Polymerase reaction is that up to one hundred fold or more nucleic acid is generated therefore increasing the level of multiplexing.

As described above, the probes include T7 RNA polymerase priming sites for this additional step. Following amplification with T7 RNA polymerase, the resulting RNA contains a zip code and a universal primer that is allele specific. The resulting material is then detected.

In one embodiment the amplicons are detected by hybridization to an array. The array can be an ordered array or a random array as described herein. In addition, the array can be a liquid array. That is, the array can be a solution-phase array and detection is accomplished in a FACS, for example. In a preferred embodiment the detection array is a random BeadArray™.

In addition to the methods outlined herein, the present invention also provides methods for accomplishing genotyping of nucleic acids, including cDNA and genomic DNA. In general, this method can be described as follows, as is generally described in WO 00/63437, hereby expressly incorporated by reference. Genomic DNA is prepared from sample cells (and generally cut into smaller segments, for example through shearing or enzymatic treatment with enzymes such as DNAse I, as is well known in the art). Using any number of techniques, as are outlined below, the genomic fragments are attached, either covalently or securely, to a support such as beads or reaction wells (eppendorf tubes, microtiter wells, etc.). Any number of different genotyping reactions can then be done as outlined below, and the reaction products from these genotyping reactions are released from the support, amplified as necessary and added to an array of capture probes as outlined herein. In general, the methods described herein relate to the detection of nucleotide substitutions, although as will be appreciated by those in the art, deletions, insertions, inversions, etc. may also be detected. Universal primers can also be included as necessary.

These genotyping techniques fall into five general categories: (1) techniques that rely on traditional hybridization methods that utilize the variation of stringency conditions (temperature, buffer conditions, etc.) to distinguish nucleotides at the detection position; (2) extension techniques that add a base ("the base") to basepair with the nucleotide at the detection position; (3) ligation techniques, that rely on the specificity of ligase enzymes (or, in some cases, on the specificity of chemical techniques), such that ligation reactions occur preferentially if perfect complementarity exists at the detection position; (4) cleavage techniques, that also rely on enzymatic or chemical specificity such that cleavage occurs preferentially if perfect complementarity exists; and (5) techniques that combine these methods. See generally WO 00/63437, incorporated by reference in its entirety.

As above, if required, the target genomic sequence is prepared using known techniques, and then attached to a solid support as defined herein. These techniques include, but are not limited to, enzymatic attachment, chemical attachment, photochemistry or thermal attachment and absorption.

In a preferred embodiment, as outlined herein, enzymatic techniques are used to attach the genomic DNA to the support. For example, terminal transferase end-labeling techniques can be used as outlined above; see Hermanson, Bioconjugate Techniques, San Diego, Academic Press, pp 640–643). In this embodiment, a nucleotide labeled with a secondary label (e.g. a binding ligand) is added to a terminus of the genomic DNA; supports coated or containing the binding partner can thus be used to immobilize the genomic DNA. Alternatively, the terminal transferase can be used to add nucleotides with special chemical functionalities that can be specifically coupled to a support. Similarly, random-primed labeling or nick-translation labeling (supra, pp. 640–643) can also be used.

In a preferred embodiment, chemical labeling (supra, pp.6444–671) can be used. In this embodiment, bisulfite-catalyzed transamination, sulfonation of cytosine residues, bromine activation of T, C and G bases, periodate oxidation of RNA or carbodiimide activation of 5' phosphates can be done.

In a preferred embodiment, photochemistry or heat-activated labeling is done (supra, p162–166). Thus for example, aryl azides and nitrenes preferably label adenosines, and to a less extent C and T (Aslam et al., Bioconjugation: Protein Coupling Techniques for Biomedical Sciences; New York, Grove's Dictionaries, 833 pp.). Psoralen or angelicin compounds can also be used (Aslam, p492, supra). The preferential modification of guanine can be accomplished via intercalation of platinum complexes (Aslam, supra).

In a preferred embodiment, the genomic DNA can be absorbed on positively charged surfaces, such as an amine coated solid phase. The genomic DNA can be cross-linked to the surface after physical absorption for increased retention (e.g. PEI coating and glutaraldehyde cross-linking; Aslam, supra, p.485).

In a preferred embodiment, direct chemical attached or photocrosslinking can be done to attach the genomic DNA to the solid phase, by using direct chemical groups on the solid phase substrate. For example, carbodiimide activation of 5' phosphates, attachment to exocyclic amines on DNA bases, and psoralen can be attached to the solid phase for crosslinking to the DNA.

Once added to the support, the target genomic sequence can be used in a variety of reactions for a variety of reasons. For example, in a preferred embodiment, genotyping reactions are done. Similarly, these reactions can also be used to detect the presence or absence of a target genomic sequence. In addition, in any reaction, quantitation of the amount of a target genomic sequence may be done. While the discussion below focuses on genotyping reactions, the discussion applies equally to detecting the presence of target sequences and/or their quantification.

As will be appreciated by those in the art, the reactions described below can take on a wide variety of formats. In one embodiment, genomic DNA is attached to a solid support, and probes comprising universal primers are added to form hybridization complexes, in a variety of formats as outlined herein. The non-hybridized probes are then removed, and the hybridization complexes are denatured This releases the probes (which frequently have been altered in some way). They are then amplified and added to an array of capture probes. In a preferred embodiment, non-hybridized primers are removed prior to the enzymatic step. Several embodiments of this have been described above. Alternatively, genomic DNA is attached to a solid support, and genotyping reactions are done in formats that can allow amplification as well, either during the genotyping reaction (e.g. through the use of heat cycling) or after, without the use of universal primers. Thus, for example, when labeled probes are used, they can be hybridized to the immobilized genomic DNA, unbound materials removed, and then eluted and collected to be added to arrays. This may be repeated for amplification purposes, with the elution fractions pooled and added to the array. In addition, alternative amplification schemes such as extending a product of the invasive cleavage reaction (described below) to include universal primers or universal primers and adapters can be performed. In one embodiment this allows the reuse of immobilized target sequences with a different set or sets of target probes.

In some embodiments, amplification of the product of the genotyping reactions is not necessary. For example, in genomes of less complexity, e.g. bacterial, yeast and Drosophila, detectable signal is achieved without the need for amplification. This is particularly true when primer extension is performed and more than one base is added to the probe, as is more fully outlined below.

In a preferred embodiment, straight hybridization methods are used to elucidate the identity of the base at the detection position. Generally speaking, these techniques break down into two basic types of reactions: those that rely on competitive hybridization techniques, and those that discriminate using stringency parameters and combinations thereof.

In a preferred embodiment, the use of competitive hybridization probes is done to elucidate either the identity of the nucleotide(s) at the detection position or the presence of a mismatch. For example, sequencing by hybridization has been described (Drmanac et al., Genomics 4:114 (1989); Koster et al., Nature Biotechnology 14:1123 (1996); U.S. Pat. Nos. 5,525,464; 5,202,231 and 5,695,940, among others, all of which are hereby expressly incorporated by reference in their entirety).

As outlined above, in a preferred embodiment, a plurality of readout probes are used to identify the base at the detection position. In this embodiment, each different readout probe comprises either a different detection label (which, as outlined below, can be either a primary label or a secondary label) or a different adapter, and a different base at the position that will hybridize to the detection position of the target sequence (herein referred to as the readout position) such that differential hybridization will occur.

Accordingly, in some embodiments, a detectable label is incorporated into the readout probe. In a preferred embodiment, a set of readout probes are used, each comprising a different base at the readout position. In some embodiments, each readout probe comprises a different label, that is distinguishable from the others. For example, a first label may be used for probes comprising adenosine at the readout position, a second label may be used for probes comprising guanine at the readout position, etc. In a preferred embodiment, the length and sequence of each readout probe is identical except for the readout position, although this need not be true in all embodiments.

The number of readout probes used will vary depending on the end use of the assay. For example, many SNPs are biallelic, and thus two readout probes, each comprising an interrogation base that will basepair with one of the detection position bases. For sequencing, for example, for the discovery of SNPs, a set of four readout probes are used, although SNPs may also be discovered with fewer readout parameters.

In one embodiment, the probes used as readout probes are "Molecular Beacon" probes as are generally described in Whitcombe et al., Nature Biotechnology 17:804 (1999), hereby incorporated by reference. As is known in the art, Molecular Beacon probes form "hairpin" type structures, with a fluorescent label on one end and a quencher on the other. In the absence of the target sequence, the ends of the hairpin hybridize, causing quenching of the label. In the presence of a target sequence, the hairpin structure is lost in favor of target sequence binding, resulting in a loss of quenching and thus an increase in signal.

In a preferred embodiment, extension genotyping is done. In this embodiment, any number of techniques are used to add a nucleotide to the readout position of a probe hybridized to the target sequence adjacent to the detection position. By relying on enzymatic specificity, preferentially a perfectly complementary base is added. All of these methods rely on the enzymatic incorporation of nucleotides at the detection position. This may be done using chain terminating dNTPs, such that only a single base is incorporated (e.g. single base extension methods), or under conditions that only a single type of nucleotide is added followed by identification of the added nucleotide (extension and pyrosequencing techniques).

In a preferred embodiment, single base extension (SBE; sometimes referred to as "minisequencing") is used to determine the identity of the base at the detection position. SBE utilizes an extension primer with at least one adapter sequence that hybridizes to the target nucleic acid immediately adjacent to the detection position, to form a hybridization complex. A polymerase (generally a DNA polymerase) is used to extend the 3' end of the primer with a nucleotide analog labeled with a detection label as described herein. Based on the fidelity of the enzyme, a nucleotide is only incorporated into the readout position of the growing nucleic acid strand if it is perfectly complementary to the base in the target strand at the detection position. The nucleotide may be derivatized such that no further extensions can occur, so only a single nucleotide is added. Once the labeled nucleotide is added, detection of the label proceeds as outlined herein. Again, amplification in this case is accomplished through cycling or repeated rounds of reaction/elution, although in some embodiments amplification is not necessary.

The reaction is initiated by introducing the hybridization complex comprising the target genomic sequence on the support to a solution comprising a first nucleotide. In general, the nucleotides comprise a detectable label, which may be either a primary or a secondary label. In addition, the nucleotides may be nucleotide analogs, depending on the configuration of the system. For example, if the dNTPs are added in sequential reactions, such that only a single type of dNTP can be added, the nucleotides need not be chain terminating. In addition, in this embodiment, the dNTPs may all comprise the same type of label.

Alternatively, if the reaction comprises more than one dNTP, the dNTPs should be chain terminating, that is, they have a blocking or protecting group at the 3' position such that no further dNTPs may be added by the enzyme. As will be appreciated by those in the art, any number of nucleotide analogs may be used, as long as a polymerase enzyme will still incorporate the nucleotide at the readout position. Preferred embodiments utilize dideoxy-triphosphate nucleotides (ddNTPs) and halogenated dNTPs. Generally, a set of nucleotides comprising ddATP, ddCTP, ddGTP and ddTTP is used, each with a different detectable label, although as outlined herein, this may not be required. Alternative preferred embodiments use acyclo nucleotides (NEN). These chain terminating nucleotide analogs are particularly good substrates for Deep vent (exo$^-$) and thermosequenase.

In addition, as will be appreciated by those in the art, the single base extension reactions of the present invention allow the precise incorporation of modified bases into a growing nucleic acid strand. Thus, any number of modified nucleotides may be incorporated for any number of reasons, including probing structure-function relationships (e.g. DNA:DNA or DNA:protein interactions), cleaving the nucleic acid, crosslinking the nucleic acid, incorporate mismatches, etc.

As will be appreciated by those in the art, the configuration of the genotyping SBE system can take on several forms.

In addition, since unextended primers do not comprise labels, the unextended primers need not be removed. However, they may be, if desired, as outlined below; for example, if a large excess of primers are used, there may not be sufficient signal from the extended primers competing for binding to the surface.

Alternatively, one of skill in the art could use a single label and temperature to determine the identity of the base; that is, the readout position of the extension primer hybridizes to a position on the capture probe. However, since the three mismatches will have lower Tms than the perfect match, the use of temperature could elucidate the identity of the detection position base.

In a preferred embodiment, the determination of the identity of the base at the detection position of the target sequence proceeds using invasive cleavage technology. As outlined above for amplification, invasive cleavage techniques rely on the use of structure-specific nucleases, where the structure can be formed as a result of the presence or absence of a mismatch. Generally, invasive cleavage technology may be described as follows. A target nucleic acid is recognized by two distinct probes. A first probe, generally referred to herein as an "invader" probe, is substantially complementary to a first portion of the target nucleic acid. A second probe, generally referred to herein as a "signal probe", is partially complementary to the target nucleic acid; the 3' end of the signal oligonucleotide is substantially complementary to the target sequence while the 5' end is non-complementary and preferably forms a single-stranded "tail" or "arm". The non-complementary end of the second probe preferably comprises a "generic" or "unique" sequence, frequently referred to herein as a "detection sequence", that is used to indicate the presence or absence of the target nucleic acid, as described below. The detection sequence of the second probe may comprise at least one detectable label (for cycling purposes), or preferably comprises one or more universal priming sites and/or an adapter sequence. Alternative methods have the detection sequence functioning as a target sequence for a capture probe, and thus rely on sandwich configurations using label probes.

Hybridization of the first and second oligonucleotides near or adjacent to one another on the target genomic nucleic acid forms a number of structures.

Accordingly, the present invention provides methods of determining the identity of a base at the detection position of a target sequence. In this embodiment, the target sequence comprises, 5' to 3', a first target domain comprising an overlap domain comprising at least a nucleotide in the detection position, and a second target domain contiguous with the detection position. A first probe (the "invader probe") is hybridized to the first target domain of the target sequence. A second probe (the "signal probe"), comprising a first portion that hybridizes to the second target domain of the target sequence and a second portion that does not hybridize to the target sequence, is hybridized to the second target domain. If the second probe comprises a base that is perfectly complementary to the detection position a cleavage structure is formed. The addition of a cleavage enzyme, such as is described in U.S. Pat. Nos. 5,846,717; 5,614,402; 5,719,029; 5,541,311 and 5,843,669, all of which are expressly incorporated by reference, results in the cleavage of the detection sequence from the signalling probe. This then can be used as a target sequence in an assay complex.

In addition, as for a variety of the techniques outlined herein, unreacted probes (i.e. signalling probes, in the case of invasive cleavage), may be removed using any number of techniques. For example, the use of a binding partner coupled to a solid support comprising the other member of the binding pair can be done. Similarly, after cleavage of the primary signal probe, the newly created cleavage products can be selectively labeled at the 3' or 5' ends using enzymatic or chemical methods.

Again, as outlined above, the detection of the invasive cleavage reaction can occur directly, in the case where the detection sequence comprises at least one label, or indirectly, using sandwich assays, through the use of additional probes; that is, the detection sequences can serve as target sequences, and detection may utilize amplification probes, capture probes, capture extender probes, label probes, and label extender probes, etc. In one embodiment, a second invasive cleavage reaction is performed on solid-phase thereby making it easier perform multiple reactions.

In addition, as for most of the techniques outlined herein, these techniques may be done for the two strands of a double-stranded target sequence. The target sequence is denatured, and two sets of probes are added: one set as outlined above for one strand of the target, and a separate set for the other strand of the target.

Thus, the invasive cleavage reaction requires, in no particular order, an invader probe, a signalling probe, and a cleavage enzyme.

It is also possible to combine two or more of these techniques to do genotyping, quantification, detection of sequences, etc., again as outlined in WO 00/63437, expressly incorporated by reference, including combinations of competitive hybridization and extension, particularly SBE; a combination of competitive hybridization and invasive cleavage; invasive cleavage and ligation; a combination of invasive cleavage and extension reactions; a combination of OLA and SBE; a combination of OLA and PCR; a combination of competitive hybridization and ligation; and a combination of competitive hybridization and invasive cleavage.

Solution Phase Assays

Alternatively, the assays of the invention can be run in solution, followed by detection of the amplicons, either by the addition of the amplicons to an array or utilizing other methods as outlined herein (mass spectroscopy, electrophoresis, etc.) as outlined herein. In this embodiment, a variety of methods can be used to remove unhybridized target probes, as outlined in WO 00/63437, expressly incorporated by reference herein.

For example, if the target analyte is not immobilized, separation methods based on the differences between single-stranded and double-stranded nucleic acids may be done. For example, there are a variety of double-stranded specific moieties known, that preferentially interact with double-stranded nucleic acids over single stranded nucleic acids. For example, there are a wide variety of intercalators known, that insert into the stacked basepairs of double stranded nucleic acid. Two of the best known examples are ethidium bromide and actinomycin D. Similarly, there are a number of major groove and minor groove binding proteins which can be used to distinguish between single stranded and double stranded nucleic acids. Similar to the poly(T) embodiment, these moieties can be attached to a support such as magnetic beads and used to preferentially bind the hybridization complexes, to remove the non-hybridized target probes and target sequences during washing steps. The hybridization complexes are then released from the beads using a denaturation step such as a thermal step.

In the case where the OLA reaction is done, an additional embodiment, depicted in FIG. 8, may be done to remove unhybridized primers. In this embodiment, a nuclease inhibitor is added to the 3' end of the downstream ligation probe, which does not comprise the adapter sequence. Thus, any nucleic acids that do not contain the inhibitors (including both the 5' unligated probe and the target sequences themselves) will be digested upon addition of a 3'-exonuclease. The ligation products are protected from exo I digestion by including, for example, 4-phosphorothioate residues at their 3' terminus, thereby, rendering them resistant to exonuclease digestion. The unligated detection oligonucleotides are not protected and are digested. Since the 5' upstream ligation probe carries the adapter sequence, the unligated downstream probe, which does carry the nuclease inhibitor and is thus also not digested, does not bind to the array and can be washed away. The nuclease inhibitors may also be used in non-OLA utilities as well.

Suitable nuclease inhibitors are known in the art and comprise thiol nucleotides. In this embodiment, suitable 3'-exonucleases include, but are not limited to, exo I, exo III, exo VII, and 3'–5' exophosphodiesterases.

Following the amplification procedure, there is present sufficient nucleic acid material to detect the results of the genotyping assays through conventional means. In the preferred embodiment, the probes used in the mutation detection reaction also contain address sequences. During the amplification process, the address sequences used to read out the results are simultaneously amplified with the mutation-detection probes. When the amplified material is applied to a detection substrate, such as an array where complementary address sequences are provided, the amplified nucleic acid probes are then detected by known methods.

In the preferred method, the detection substrate is a random array substrate, as described in U.S. Pat. No. 6,023,540 which is incorporated by reference herein, where the hybridization of complementary nucleic acid sequences, or address sequences, are used as the particular detection means. The arrays can be manufactured with a standard set of nucleic acid address sequences, one address sequence for each different nucleic acid to be detected. The complementary nucleic acid sequences are provided as part of the linear nucleic acid sequences of the mutation-detection probes, inside of the working portion of the amplification primers. During amplification, the address sequences are amplified along with each respective mutation-detection probe. In order to detect the results of the multiplexed genotyping reaction, the resulting amplified mutation-detection probe mixture is applied to the array, whereby the complementary address sequences on the mutation-detection probes and on the array hybridize, and the results are analyzed by known methods, such as fluorescence.

Other detection schemes such as flow cytometry, mass spectroscopy, spotted arrays, or spatially-directed arrays can also be used to simultaneously read the results of the multiplexed nucleic acid detection reactions.

Accordingly, the present invention provides methods and compositions useful in the detection of nucleic acids, particularly the labeled amplicons outlined herein. As is more fully outlined below, preferred systems of the invention work as follows. Amplicons are attached (via hybridization) to an array site. This attachment can be either directly to a capture probe on the surface, through the use of adapters, or indirectly, using capture extender probes as outlined herein. In some embodiments, the target sequence itself comprises the labels. Alternatively, a label probe is then added, forming an assay complex. The attachment of the label probe may be direct (i.e. hybridization to a portion of the target sequence), or indirect (i.e. hybridization to an amplifier probe that hybridizes to the target sequence), with all the required nucleic acids forming an assay complex.

Accordingly, the present invention provides array compositions comprising at least a first substrate with a surface comprising individual sites. By "array" or "biochip" herein is meant a plurality of nucleic acids in an array format; the size of the array will depend on the composition and end use of the array. Nucleic acids arrays are known in the art, and can be classified in a number of ways; both ordered arrays (e.g. the ability to resolve chemistries at discrete sites), and random arrays are included. Ordered arrays include, but are not limited to, those made using photolithography techniques (Affymetrix GeneChip™), spotting techniques (Synteni and others), printing techniques (Hewlett Packard and Rosetta), three dimensional "gel pad" arrays, etc. A preferred embodiment utilizes microspheres on a variety of substrates including fiber optic bundles, as are outlined in PCTs US98/21193, PCT US99/14387 and PCT US98/05025; WO98/50782; and U.S. Ser. Nos. 09/287,573, 09/151,877, 09/256,943, 09/316,154, 60/119,323, 09/315,584; all of which are expressly incorporated by reference.

Arrays containing from about 2 different bioactive agents (e.g. different beads, when beads are used) to many millions can be made, with very large arrays being possible. Generally, the array will comprise from two to as many as a billion or more, depending on the size of the beads and the substrate, as well as the end use of the array, thus very high density, high density, moderate density, low density and very low density arrays may be made. Preferred ranges for very high density arrays are from about 10,000,000 to about 2,000,000,000, with from about 100,000,000 to about 1,000,000,000 being preferred (all numbers being in square cm). High density arrays range about 100,000 to about 10,000,000, with from about 1,000,000 to about 5,000,000 being particularly preferred. Moderate density arrays range from about 10,000 to about 100,000 being particularly preferred, and from about 20,000 to about 50,000 being especially preferred. Low density arrays are generally less than 10,000, with from about 1,000 to about 5,000 being preferred. Very low density arrays are less than 1,000, with from about 10 to about 1000 being preferred, and from about 100 to about 500 being particularly preferred. In some embodiments, the compositions of the invention may not be in array format; that is, for some embodiments, compositions comprising a single bioactive agent may be made as well. In addition, in some arrays, multiple substrates may be used, either of different or identical compositions. Thus for example, large arrays may comprise a plurality of smaller substrates.

In addition, one advantage of the present compositions is that particularly through the use of fiber optic technology, extremely high density arrays can be made. Thus for example, because beads of 200 $\mu$m or less (with beads of 200 nm possible) can be used, and very small fibers are known, it is possible to have as many as 40,000 or more (in some instances, 1 million) different elements (e.g. fibers and beads) in a 1 mm$^2$ fiber optic bundle, with densities of greater than 25,000,000 individual beads and fibers (again, in some instances as many as 50–100 million) per 0.5 cm$^2$ obtainable (4 million per square cm for 5$\mu$ center-to-center and 100 million per square cm for 1$\mu$ center-to-center).

By "substrate", "array substrate" or "solid support" or other grammatical equivalents herein is meant any material that can be modified to contain discrete individual sites appropriate for the attachment or association of beads and is amenable to at least one detection method. It should be noted that the array substrate is distinct from the "capture surface" described above. The capture surface is for the immobilization of target nucleic acids while the array substrate is for detection of amplicons, i.e. the results of the detection or genotyping assay. As will be appreciated by those in the art, the number of possible array substrates is very large. Possible array substrates include, but are not limited to, glass and modified or functionalized glass, plastics (including acrylics, polystyrene and copolymers of styrene and other materials, polypropylene, polyethylene, polybutylene, polyurethanes, Teflon, etc.), polysaccharides, nylon or nitrocellulose, resins, silica or silica-based materials including silicon and modified silicon, carbon, metals, inorganic glasses, plastics, optical fiber bundles, and a variety of other polymers. In general, the array substrates allow optical detection and do not themselves appreciably fluoresce.

Generally the array substrate is flat (planar), although as will be appreciated by those in the art, other configurations of substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. Preferred substrates include optical fiber bundles as discussed below, and flat planar substrates such as paper, glass, polystyrene and other plastics and acrylics.

In a preferred embodiment, the substrate is an optical fiber bundle or array, as is generally described in U.S. Ser. Nos. 08/944,850 and 08/519,062, PCT US98/05025, and PCT US98/09163, all of which are expressly incorporated herein by reference. Preferred embodiments utilize preformed unitary fiber optic arrays. By "preformed unitary fiber optic array" herein is meant an array of discrete individual fiber optic strands that are co-axially disposed and joined along their lengths. The fiber strands are generally individually clad. However, one thing that distinguished a preformed unitary array from other fiber optic formats is that the fibers are not individually physically manipulatable; that is, one strand generally cannot be physically separated at any point along its length from another fiber strand.

Generally, the array of array compositions of the invention can be configured in several ways; see for example U.S. Ser. No. 09/473,904, hereby expressly incorporated by reference. In a preferred embodiment, as is more fully outlined below, a "one component" system is used. That is, a first substrate comprising a plurality of assay locations (sometimes also referred to herein as "assay wells"), such as a microtiter plate, is configured such that each assay location contains an individual array. That is, the assay location and the array location are the same. For example, the plastic material of the microtiter plate can be formed to contain a plurality of "bead wells" in the bottom of each of the assay wells. Beads containing the capture probes of the invention can then be loaded into the bead wells in each assay location as is more fully described below. Arrays are described in U.S. Pat. No. 6,023,540 and U.S. Ser. No. 09/151,877, filed Sep. 11, 1998, Ser. No. 09/450,829, filed Nov. 29, 1999, Ser. No. 09/816,651, filed Mar. 23, 2001, and Ser. No. 09/840,012, filed Apr. 20, 2001, all of which are expressly incorporated herein by reference. In addition, other arrays are described in No. 60/181,631, filed Feb. 10, 2000, Ser. No. 09/782,588, filed Feb. 12, 2001, Ser. No. 60/113,968, filed Dec. 28, 1998, Ser. No. 090/256,943, filed Feb. 24, 1999, Ser. No. 09/473,904, filed Dec. 28, 1999 and Ser. No. 09/606,369, filed Jun. 28, 2000, all of which are expressly incorporated herein by reference.

Alternatively, a "two component" system can be used. In this embodiment, the individual arrays are formed on a second substrate, which then can be fitted or "dipped" into the first microtiter plate substrate. A preferred embodiment utilizes fiber optic bundles as the individual arrays, generally with "bead wells" etched into one surface of each individual fiber, such that the beads containing the capture probes are loaded onto the end of the fiber optic bundle. The composite array thus comprises a number of individual arrays that are configured to fit within the wells of a microtiter plate.

By "composite array" or "combination array" or grammatical equivalents herein is meant a plurality of individual arrays, as outlined above. Generally the number of individual arrays is set by the size of the microtiter plate used; thus, 96 well, 384 well and 1536 well microtiter plates utilize composite arrays comprising 96, 384 and 1536 individual arrays, although as will be appreciated by those in the art, not each microtiter well need contain an individual array. It should be noted that the composite arrays can comprise individual arrays that are identical, similar or different. That is, in some embodiments, it may be desirable to do the same 2,000 assays on 96 different samples; alternatively, doing 192,000 experiments on the same sample (i.e. the same sample in each of the 96 wells) may be desirable. Alternatively, each row or column of the composite array could be the same, for redundancy/quality control. As will be appreciated by those in the art, there are a variety of ways to configure the system. In addition, the random nature of the arrays may mean that the same population of beads may be added to two different surfaces, resulting in substantially similar but perhaps not identical arrays.

At least one surface of the substrate is modified to contain discrete, individual sites for later association of microspheres. These sites may comprise physically altered sites, i.e. physical configurations such as wells or small depressions in the substrate that can retain the beads, such that a microsphere can rest in the well, or the use of other forces (magnetic or compressive), or chemically altered or active sites, such as chemically functionalized sites, electrostatically altered sites, hydrophobically/hydrophilically functionalized sites, spots of adhesive, etc.

The sites may be a pattern, i.e. a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of beads on the substrate. However, it should be noted that these sites may not be discrete sites. That is, it is possible to use a uniform surface of adhesive or chemical functionalities, for example, that allows the attachment of beads at any position. That is, the surface of the substrate is modified to allow attachment of the microspheres at individual sites, whether or not those sites are contiguous or non-contiguous with other sites. Thus, the surface of the substrate may be modified such that discrete sites are formed that can only have a single associated bead, or alternatively, the surface of the substrate is modified and beads may go down anywhere, but they end up at discrete sites. That is, while beads need not occupy each site on the array, no more than one bead occupies each site.

In a preferred embodiment, the surface of the substrate is modified to contain wells, i.e. depressions in the surface of the substrate. This may be done as is generally known in the art using a variety of techniques, including, but not limited to, photolithography, stamping techniques, molding techniques and microetching techniques. As will be appreciated by those in the art, the technique used will depend on the composition and shape of the substrate.

In a preferred embodiment, physical alterations are made in a surface of the substrate to produce the sites. In a preferred embodiment, the substrate is a fiber optic bundle and the surface of the substrate is a terminal end of the fiber bundle, as is generally described in Ser. No. 08/818,199 and Ser. No. 09/151,877, both of which are hereby expressly incorporated by reference. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells.

Generally in this embodiment, the microspheres are non-covalently associated in the wells, although the wells may additionally be chemically functionalized as is generally described below, cross-linking agents may be used, or a physical barrier may be used, i.e. a film or membrane over the beads.

In a preferred embodiment, the surface of the substrate is modified to contain chemically modified sites, that can be used to attach, either covalently or non-covalently, the microspheres of the invention to the discrete sites or locations on the substrate. "Chemically modified sites" in this context includes, but is not limited to, the addition of a pattern of chemical functional groups including amino groups, carboxy groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic attachment of the microspheres, i.e. when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites. As outlined above, "pattern" in this sense includes the use of a uniform treatment of the surface to allow attachment of the beads at discrete sites, as well as treatment of the surface resulting in discrete sites. As will be appreciated by those in the art, this may be accomplished in a variety of ways.

In some embodiments, the beads are not associated with a substrate. That is, the beads are in solution or are not distributed on a patterned substrate.

In a preferred embodiment, the compositions of the invention further comprise a population of microspheres. By "population" herein is meant a plurality of beads as outlined above for arrays. Within the population are separate subpopulations, which can be a single microsphere or multiple identical microspheres. That is, in some embodiments, as is more fully outlined below, the array may contain only a single bead for each capture probe; preferred embodiments utilize a plurality of beads of each type.

By "microspheres" or "beads" or "particles" or grammatical equivalents herein is meant small discrete particles. The composition of the beads will vary, depending on the class of capture probe and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon may all be used. "*Microsphere Detection Guide*" from Bangs Laboratories, Fishers Ind. is a helpful guide.

The beads need not be spherical; irregular particles may be used. In addition, the beads may be porous, thus increasing the surface area of the bead available for either capture probe attachment or tag attachment. The bead sizes range from nanometers, i.e. 100 nm, to millimeters, i.e. 1 mm, with beads from about 0.2 micron to about 200 microns being preferred, and from about 0.5 to about 5 micron being particularly preferred, although in some embodiments smaller beads may be used.

Each microsphere comprises a capture probe, although as will be appreciated by those in the art, there may be some microspheres which do not contain a capture probe, depending on the synthetic methods.

Attachment of the nucleic acids may be done in a variety of ways, as will be appreciated by those in the art, including, but not limited to, chemical or affinity capture (for example, including the incorporation of derivatized nucleotides such as AminoLink or biotinylated nucleotides that can then be used to attach the nucleic acid to a surface, as well as affinity capture by hybridization), cross-linking, and electrostatic attachment, etc. In a preferred embodiment, affinity capture is used to attach the nucleic acids to the beads. For example, nucleic acids can be derivatized, for example with one member of a binding pair, and the beads derivatized with the other member of a binding pair. Suitable binding pairs are as described herein for IBL/DBL pairs. For example, the nucleic acids may be biotinylated (for example using enzymatic incorporate of biotinylated nucleotides, for by photoactivated cross-linking of biotin). Biotinylated nucleic acids can then be captured on streptavidin-coated beads, as is known in the art. Similarly, other hapten-receptor combinations can be used, such as digoxigenin and anti-digoxigenin antibodies. Alternatively, chemical groups can be added in the form of derivatized nucleotides, that can them be used to add the nucleic acid to the surface.

Similarly, affinity capture utilizing hybridization can be used to attach nucleic acids to beads.

Alternatively, chemical crosslinking may be done, for example by photoactivated crosslinking of thymidine to reactive groups, as is known in the art.

In a preferred embodiment, each bead comprises a single type of capture probe, although a plurality of individual capture probes are preferably attached to each bead. Similarly, preferred embodiments utilize more than one microsphere containing a unique capture probe; that is, there is redundancy built into the system by the use of subpopulations of microspheres, each microsphere in the subpopulation containing the same capture probe.

As will be appreciated by those in the art, the capture probes may either be synthesized directly on the beads, or they may be made and then attached after synthesis. In a preferred embodiment, linkers are used to attach the capture probes to the beads, to allow both good attachment, sufficient flexibility to allow good interaction with the target molecule, and to avoid undesirable binding reactions.

In a preferred embodiment, the capture probes are synthesized directly on the beads. As is known in the art, many classes of chemical compounds are currently synthesized on solid supports, such as peptides, organic moieties, and nucleic acids. It is a relatively straightforward matter to adjust the current synthetic techniques to use beads.

In a preferred embodiment, the capture probes are synthesized first, and then covalently attached to the beads. As will be appreciated by those in the art, this will be done depending on the composition of the capture probes and the beads. The functionalization of solid support surfaces such as certain polymers with chemically reactive groups such as thiols, amines, carboxyls, etc. is generally known in the art. Accordingly, "blank" microspheres may be used that have surface chemistries that facilitate the attachment of the desired functionality by the user. Some examples of these surface chemistries for blank microspheres include, but are not limited to, amino groups including aliphatic and aromatic amines, carboxylic acids, aldehydes, amides, chloromethyl groups, hydrazide, hydroxyl groups, sulfonates and sulfates.

When random arrays or liquid arrays are used, an encoding/decoding system must be used. For example, when microsphere arrays are used, the beads are generally put onto the substrate randomly; as such there are several ways to correlate the functionality on the bead with its location, including the incorporation of unique optical signatures, generally fluorescent dyes, that could be used to identify the nucleic acid on any particular bead. This allows the synthesis of the capture probes to be divorced from their placement on an array, i.e. the capture probes may be synthesized on the beads, and then the beads are randomly distributed on a patterned surface. Since the beads are first coded with an optical signature, this means that the array can later be "decoded", i.e. after the array is made, a correlation of the location of an individual site on the array with the bead or probe at that particular site can be made. This means that the beads may be randomly distributed on the array, a fast and inexpensive process as compared to either the in situ synthesis or spotting techniques of the prior art.

When liquid arrays are used, beads to which the amplicons are immobilized can be analyzed by FACS. Again, beads can be decoded to determine which amplicon is immobilized on the bead. This is an indication of the presence of the target analyte.

However, the drawback to these methods is that for a large array, the system requires a large number of different optical signatures, which may be difficult or time-consuming to utilize. Accordingly, methods for analysis and decoding of arrays are described in Ser. No. 08/944,850, filed Oct. 6, 1997, PCT/US98/21193, filed Oct. 6, 1998, Ser. No. 09/287,573, filed Apr. 6, 1999, PCT/US00/09183, filed May 6, 2000, No. 60/238,866, filed Oct. 6, 2000, No. 60/119,323, filed Feb. 9, 1999, Ser. No. 09/500,555, filed Feb. 9, 2000, Ser. No. 09/636,387, filed Aug. 9, 2000, No. 60/151,483, filed Aug. 30, 1999, No. 60/151,668, filed Aug. 31, 1999, Ser. No. 09/651,181, filed Aug. 30, 2000, No. 60/272,803, filed Mar. 1, 2001, all of which are expressly incorporated herein by reference. In addition, methods of decoding arrays are described in No. 60/090,473, filed Jun. 24, 1998, Ser. No. 09/189,543, filed Nov. 10, 1998, Ser. No. 09/344,526, filed Jun. 24, 1999, PCT/US99/14387, filed Jun. 24, 1999, No. 60/172, 106, filed Dec. 23, 1999, No. 60/235,531, filed Sep. 26, 2000, Ser. No. 09/748,706, filed Dec. 22, 2000, and provisional application entitled Decoding of Array Sensors with Microspheres, filed Jun. 28, 2001 (no serial number received), all of which are expressly incorporated herein by reference.

As outlined herein, the present invention finds use in a wide variety of applications. All references cited herein are incorporated by reference.

EXAMPLES

Attachment of Genomic DNA to a Solid Support
1. Fragmentation of Genomic DNA

| Human Genomic DNA | 10 mg (100 µl) |
|---|---|
| 10 × DNase I Buffer | 12.5 µl |
| DNase I (1 U/µl, BRL) | 0.5 µl |
| ddH2O | 12 µl |

Incubate 37° C. for 10 min. Add 1.25 µl 0.5 M EDTA, Heat at 99° C. for 15 min.
2. Precipitation of Fragmented Genomic DNA

| DNase I fragmented genomic DNA | 125 µl |
|---|---|
| Quick-Precip Plus Solution (Edge Biosystems) | 20 µl |
| Cold 100% EtOH | 300 µl |

Store at −20° C. for 20 min. Spin at 12,500 rpm for 5 min. Wash pellet 2× with 70% EtOH, and air dry.
3. Terminal Transferase End-Labeling with Biotin

| DNase I fragmented and precipitated genomic DNA (in H2O) | 77.3 µl |
|---|---|
| 5 × Terminal transferase buffer | 20 µl |
| Biotin-N6-ddATP (1 mM, NEN) | 1 µl |
| Terminal transferase (15 U/µl) | 1.7 µl |

37° C. for 60 min. Add 1µl 0.5 M EDTA, then heat at 99° C. for 15 min
4. Precipitation of Biotin-Labeled Genomic DNA

| Biotin-labeled genomic DNA | 100 µl |
|---|---|
| Quick-Precip Solution | 20 µl |
| EtOH | 250 µl |

−20° C. for 20 min and spin at 12,500 rpm for 5 min, wash 2× with 70% EtOH and air dry.
5. Immobilization of Biotin-Labeled Genomic DNA to Streptavidin-Coated PCR Tubes Heat-denature genomic DNA for 10 min on 95° C. heat block.

| Biotin-labeled genomic DNA (0.3 µg/µl) | 3 µl |
|---|---|
| 2 × binding buffer | 25 µl |
| SNP Primers (50 nM) | 10 µl |
| ddH2O | 12 µl |

Incubate at 60° C. for 60 min.
Wash 133 with 1× binding buffer,
1× with 1× washing buffer,
1× with 1× ligation buffer.
1× binding buffer: 20 mM Tris-HCl, pH7.5, 0.5M NaCl, 1 mM EDTA, 0.1% SDS.
1× washing buffer: 20 mM Tris-HCl pH7.5, 0.1 M NaCl, 1mM EDTA, 0.1% Triton X-100.
1× ligation buffer: 20 mM Tris-HCl pH7.6, 25 mM Potassium acetate, 10 mM magnesium acetate, 10 mM DTT, 1 mM NAD, 0.1% Triton X-100.

6. Ligation in Streptavidin-Coated PCR Tubes

| make a master solution and each tube contains | 49 μl 1 × ligation buffer<br>1 μl Taq DNA Ligase (40 U/μl) |
|---|---| incubate at 60° C. for 60 min.

| wash each tube | 1× with 1× washing buffer<br>1× with ddH2O |
|---|---|

7. Elution of Ligated Products
add 50 μl ddH2O to each tube and incubated at 95° C. for 5 min, chilled on ice, transfer the supernatant to a clean tube.
8. PCR Set Up

| 25 mM dNTPs | 0.5 μl |
|---|---|
| 10 × buffer II (PEB) | 2.5 μl |
| 25 mM MgCl2 | 1.5 μl |
| AmpliTaq Gold DNA Polymerase (5 Units/μl, PEB) | 0.3 μl |
| Eluted (ligated) product (see above) | 3 μl |
| Primer set (T3/T7/T7v, 10 μM each) | 2 μl |
| ddH2O | 1 μl |
| Total volume | 25 μl |

PCR condition:
94° C. 10 min
35 cycles of 94° C. 30 sec
60° C. 30 sec
and then
72° C. 30 sec

What is claimed is:

1. A method of detecting at least first and second target molecules in a sample comprising:
   a) contacting said first and second target molecule with a composition comprising:
      i) an amplification enzyme; and
      ii) first and second target probes, said first and second target probes comprising:
         (a) a first and a second bioactive agent, respectively, wherein said first and second bioactive agents specifically bind to said first and second target molecules, respectively;
         (b) a first and a second adapter sequence, respectively, wherein said first adapter sequence identifies said first target molecule and said second adapter sequence identifies said second target molecule; and
         (c) at least a first and a second upstream universal priming sequences;
   b) amplifying said first and second adapter sequences using said first and second universal priming sequences, wherein no ligation is performed, to form first and second amplicons, respectively;
   c) detecting said first and second amplicons, respectively, to indicate the presence of said first and second target molecules in said sample.

2. The method according to claim 1, wherein said first and second target molecules are selected from the group consisting of proteins and nucleic acids.

3. The method according to claim 2, wherein said first and second target molecules are nucleic acids.

4. The method according to claim 3, wherein said first and second bioactive agents are first and second target specific domains that are substantially complementary to at least one domain of said first and second target nucleic acids, respectively.

5. The method according to claim 4, wherein said first and second target nucleic acids further comprise a first and second detection position, respectively, and said first and second target specific domains comprise a nucleotide at a readout position that is perfectly complementary to the nucleotide at said first and second detection positions.

6. The method according to claim 4, wherein said first and second upstream universal priming sequences are RNA Polymerase primers and said enzyme is a RNA Polymerase.

7. The method according to claim 6, wherein said RNA Polymerase primers are T7 primers.

8. The method according to claim 4, further comprising contacting said first and second upstream universal priming sequences with first and second chimeric RNA/DNA primers, prior to said amplifying.

9. The method according to claim 4, wherein said first and second target probes further comprise first and second downstream universal priming sequences, wherein said first and second upstream universal priming sequences and said first and second downstream universal priming sequences flank said first and second adapter sequences, respectively.

10. The method according to claim 9 further comprising contacting said first and second upstream universal priming sequences and said first and second downstream universal priming sequences with first and second universal primers, wherein said amplification is by PCR.

11. The method according to claim 2, wherein said first and second target molecules are proteins.

12. The method according to claim 11, wherein at least said first bioactive agent is an antibody.

13. The method according to claim 11, wherein at least said first bioactive agent is a ligand.

14. The method according to claim 11, wherein at least said first bioactive agent is an aptamer.

15. The method according to claim 11, wherein said first and second upstream universal priming sequences are RNA Polymerase primers and said enzyme is a RNA Polymerase.

16. The method according to claim 15, wherein said first and second upstream universal priming sequences are T7 RNA Polymerase primers.

17. The method according to claim 11, further comprising contacting said first and second upstream universal priming sequences with first and second chimeric RNA/DNA primers, respectively, prior to said amplifying.

18. The method according to claim 11, wherein said first and second target probes further comprise first and second downstream universal priming sequences, wherein said first and second upstream universal priming sequences and said first and second downstream universal priming sequences flank said first and second adapter sequences, respectively.

19. The method according to claim 1, wherein said composition further comprises nucleotides.

20. The method according to claim 19, wherein at least said one of nucleotides are labeled nucleotides.

21. The method according to claim 1, wherein said detecting comprises:
   a) contacting said first and second amplicons with at least one substrate comprising first and second capture probes, wherein said first capture probes are complementary to said first adapters and said second capture probes are complementary to said second adapters; and
   b) detecting said first and second amplicons on said at least one substrate.

22. The method according to claim 21, wherein said substrate comprises an array, said array comprising at least first and second capture probes immobilized on said substrate.

23. The method according to claim 22, wherein said array is an ordered array.

24. The method according to claim 21, wherein said substrate comprises at least a first and a second population of microspheres, wherein said first capture probes are immobilized on said first population of microspheres and said second capture probes are immobilized on said second population of microspheres.

25. The method according to claim 24, wherein said first and second amplicons are detected in a liquid array.

26. The method according to claim 25, wherein said first and second amplicons are detected by FACS.

27. The method according to claim 24, wherein said microspheres are randomly distributed on a second substrate comprising discrete sites.

28. The method according to claim 24, wherein said microspheres are applied to a mass spectrometer and the mass of said adapter sequence is determined to identify the presence of said first and second target molecules.

29. A method for multiplex detection of a plurality of target molecules in a sample, said method comprising;
   a) contacting said plurality of target molecules with a composition comprising
      a plurality of target probes, each comprising:
         i) a bioactive agent, wherein each bioactive agent binds to a unique target molecule;
         ii) an adapter sequence that identifies said unique target molecule that binds the bioactive agent; and
         iii) at least one upstream universal priming sequence;
   b) removing unbound target probes, leaving bound target probes;
   c) contacting said bound target probes with an amplification enzyme;
   d) amplifying said adapter sequences of said bound target probes using said at least one universal priming sequence, wherein no ligation is performed, to form a plurality of amplicons;
   e) detecting said plurality of amplicons, to indicate the presence of said target molecules in said sample.

30. The method according to claim 29, wherein said target molecules are selected from the group consisting of proteins and nucleic acids.

31. The method according to claim 30, wherein said target molecules are proteins.

32. The method according to claim 30, wherein said target molecules are nucleic acids.

33. The method according to claim 29 or 30, wherein said plurality of target molecules comprises at least 500 target molecules.

34. The method according to claim 29 or 30, wherein said plurality of target molecules comprises at least 1000 target molecules.

* * * * *